(12) United States Patent
Lee et al.

(10) Patent No.: US 9,782,486 B2
(45) Date of Patent: Oct. 10, 2017

(54) ALBUMIN CONJUGATED TEMPERATURE AND PH-SENSITIVE MULTI-BLOCK COPOLYMER, A METHOD OF PREPARATION THEREOF AND DRUG DELIVERY SYSTEM USING THE SAME

(71) Applicant: Research & Business Foundation Sungkyunkwan University, Suwon-si (KR)

(72) Inventors: Doo Sung Lee, Suwon-si (KR); Kiattikhun Manokruang, Chiang Mai (TH); Bong Sup Kim, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 14/574,720

(22) Filed: Dec. 18, 2014

(65) Prior Publication Data

US 2016/0022823 A1    Jan. 28, 2016

(30) Foreign Application Priority Data

Jul. 28, 2014    (KR) ........................ 10-2014-0095998

(51) Int. Cl.
*A61K 47/42*    (2017.01)
*A61K 38/47*    (2006.01)
(Continued)

(52) U.S. Cl.
CPC ............ *A61K 47/42* (2013.01); *A61K 9/0024* (2013.01); *A61K 31/704* (2013.01); *A61K 38/47* (2013.01); *A61K 47/32* (2013.01); *A61K 47/34* (2013.01); *C08F 283/006* (2013.01); *C08G 18/3293* (2013.01); *C08G 18/3844* (2013.01);
(Continued)

(58) Field of Classification Search
CPC ...................................................... A61K 47/42
See application file for complete search history.

(56) References Cited

U.S. PATENT DOCUMENTS 5,476,909 A    12/1995    Kim et al.
6,004,573 A    12/1999    Rathi et al.

FOREIGN PATENT DOCUMENTS

IL    WO 2010064252 A2 *    6/2010    ........... A61K 9/0024
KR    10-0665672 B1    1/2007
(Continued)

OTHER PUBLICATIONS

Nguyen et al (Macromol. Biosci. Oct. 2010, 563-579).*
(Continued)

*Primary Examiner* — Benjamin Packard
(74) *Attorney, Agent, or Firm* — NSIP Law

(57) ABSTRACT

The present invention relates to a conjugate of albumin and a temperature- and pH-sensitive multi-block copolymer, a method of preparation thereof, and a sustained-release drug carrier comprising the same, and more specifically, to a conjugate in which polyethylene glycol-poly(amino urethane) (PEG-PAU) or polyethylene glycol-poly(amino ester urethane) (PEG-PAEU) multi-block copolymer is conjugated to albumin, a method of preparing the same, and a long-term sustained-release drug carrier comprising the same, capable of reducing an initial burst release of drugs and improving an affinity to drugs.

14 Claims, 13 Drawing Sheets

(51) Int. Cl.
- A61K 31/704 (2006.01)
- A61K 9/00 (2006.01)
- A61K 47/32 (2006.01)
- A61K 47/34 (2017.01)
- C08G 18/48 (2006.01)
- C08G 18/66 (2006.01)
- C08G 18/73 (2006.01)
- C08G 18/83 (2006.01)
- C08F 283/00 (2006.01)
- C08G 18/32 (2006.01)
- C08G 18/38 (2006.01)
- A61K 9/06 (2006.01)
- A61K 38/00 (2006.01)

(52) U.S. Cl.
CPC ..... *C08G 18/4833* (2013.01); *C08G 18/6666* (2013.01); *C08G 18/6688* (2013.01); *C08G 18/73* (2013.01); *C08G 18/831* (2013.01); *A61K 9/06* (2013.01); *A61K 38/00* (2013.01); *C12Y 302/01017* (2013.01)

(56) References Cited

FOREIGN PATENT DOCUMENTS

| KR | 10-2006-0071412 A | 7/2012 |
| KR | 10-2012-0096768 A | 8/2012 |
| KR | 10-2014-0006271 A | 1/2014 |

OTHER PUBLICATIONS

Greenwald, Richard B., et al. "Effective drug delivery by PEGylated drug conjugates." Advanced drug delivery reviews 55.2 (2003): 217-250.

Dayananda, Kasala, et al. "pH-and temperature-sensitive multiblock copolymer hydrogels composed of poly (ethylene glycol) and poly (amino urethane)." Polymer 49.23 (2008): 4968-4973.

Oss-Ronen, Liat, et al. "Polymer-conjugated albumin and fibrinogen composite hydrogels as cell scaffolds designed for affinity-based drug delivery." Acta biomaterialia 7.1 (2011): 163-170.

Manokruang, Kiattikhun, et al. "Albumin-Conjugated pH/Thermo Responsive Poly (amino urethane) Multiblock Copolymer as an Injectable Hydrogel for Protein Delivery." Macromolecular bioscience 13.9 (2013): 1195-1203.

Manokruang, Kiattikhun, et al. "Injectable hydrogels based on poly (amino urethane) conjugated bovine serum albumin." Materials Letters 124 (2014): 105-109.

Dong Kook Park, "Studies on pH-Sensitive Block Copolymer for Drug Carrier." (Master's Thesis) Sungkyunkwan University, Oct. 2008, p. 1-48. (30 pages in English).

Huynh, Cong Truc, et al. "Synthesis and characterization of poly (amino urea urethane)-based block copolymer and its potential application as injectable pH/temperature-sensitive hydrogel for protein carrier." Polymer 53.19 (2012): 4069-4075. (7 pages in English).

\* cited by examiner

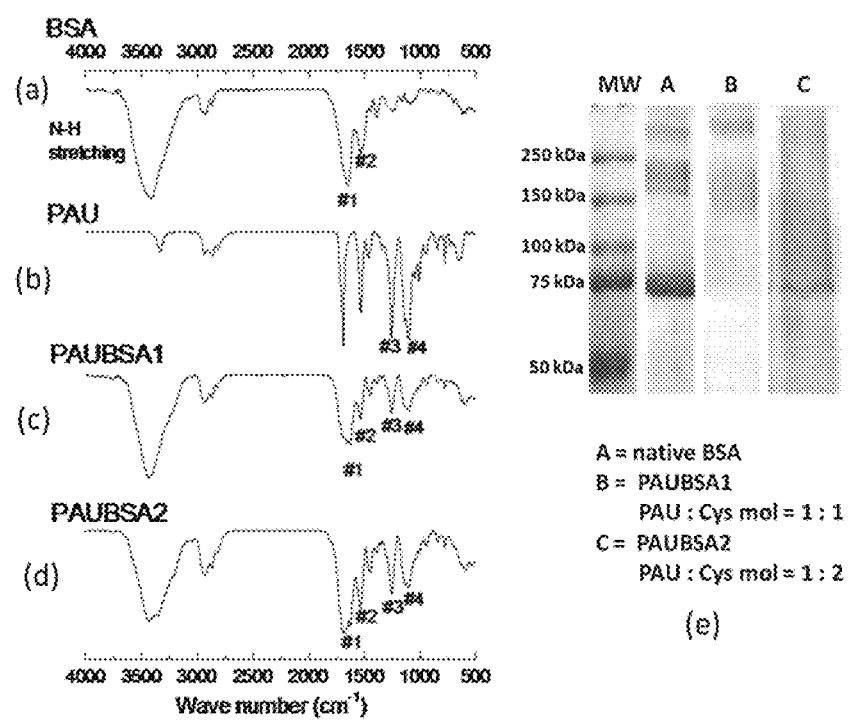

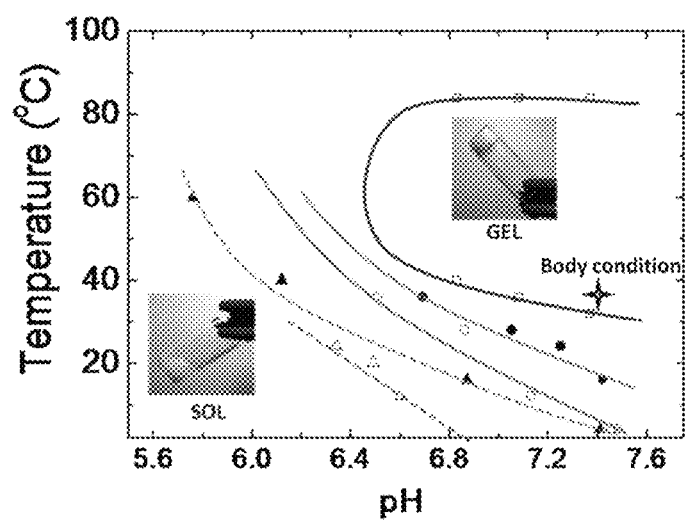
[FIG. 2]

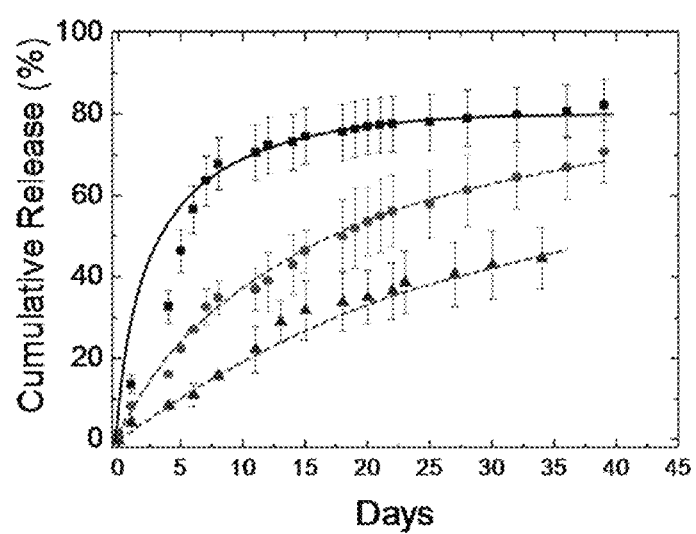

[FIG. 4]
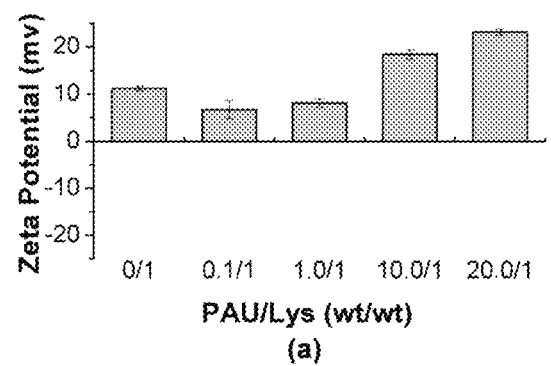
(a)
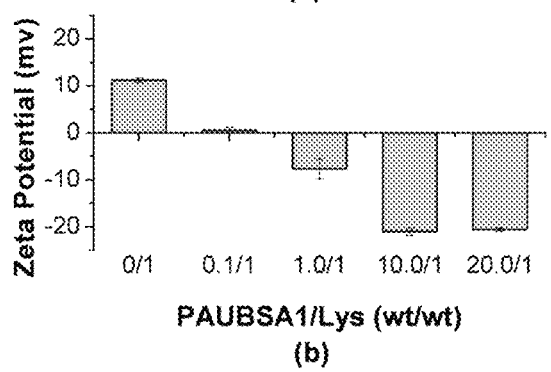
(b)

[FIG. 5]
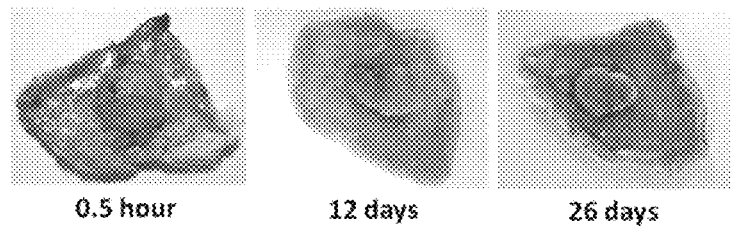
0.5 hour　　　12 days　　　26 days

[FIG. 6]
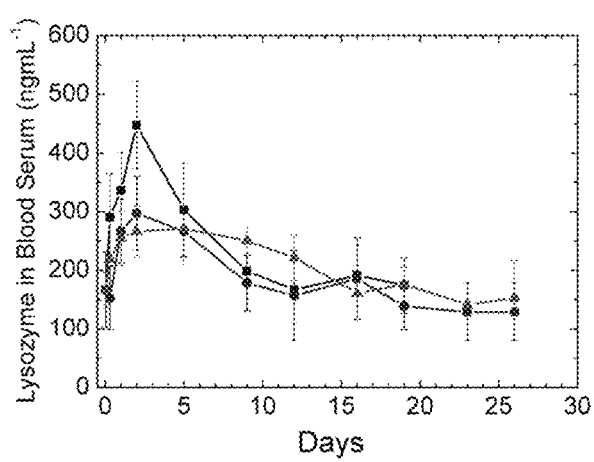

[FIG. 7]
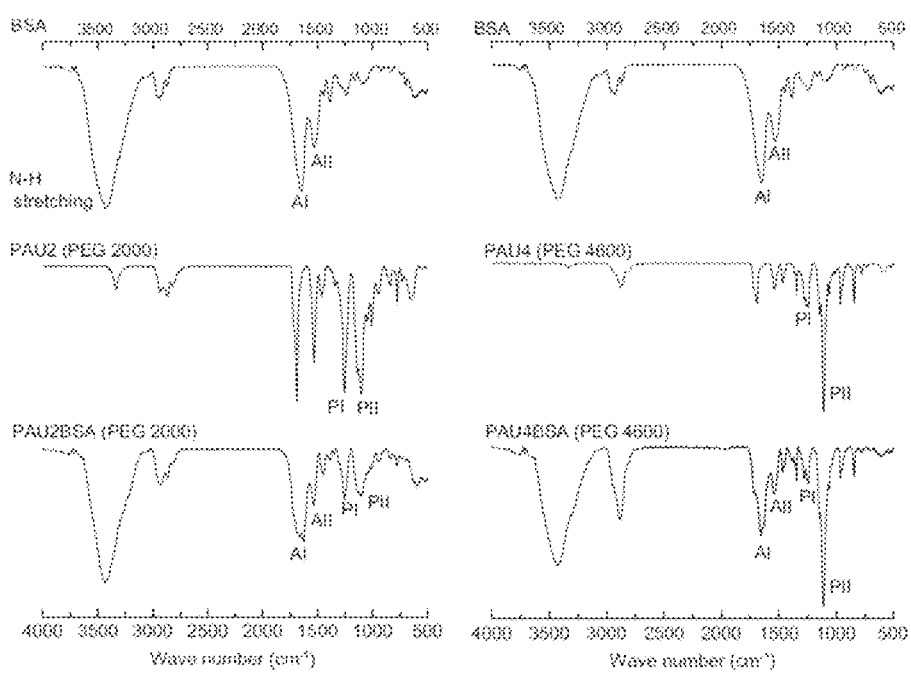

[FIG. 8]
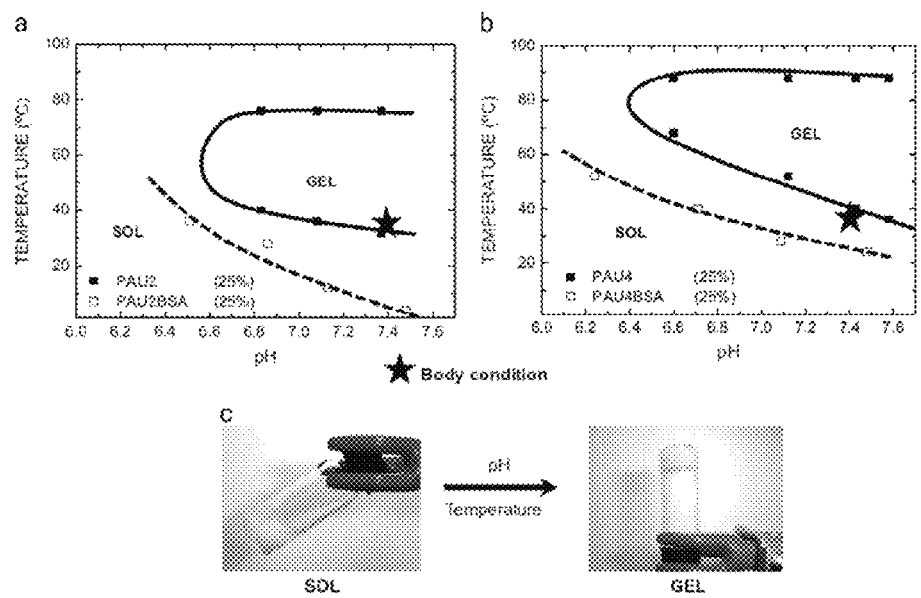

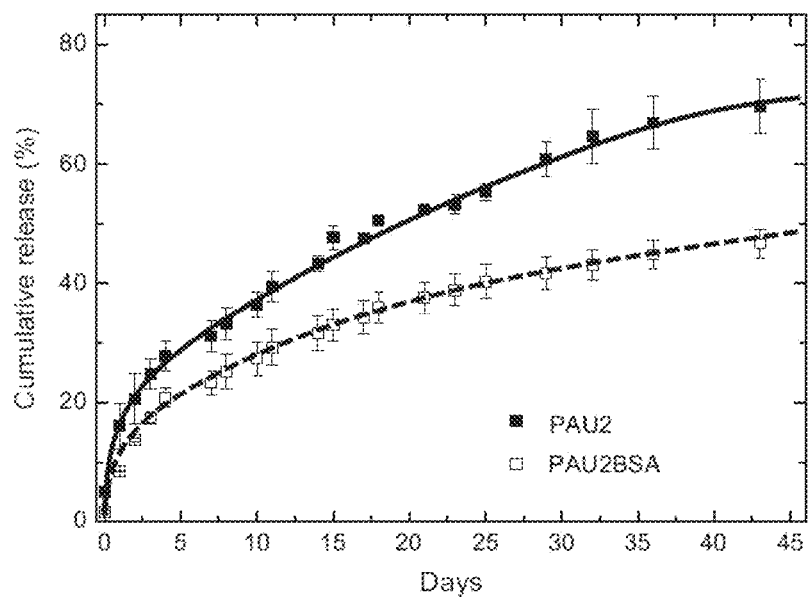

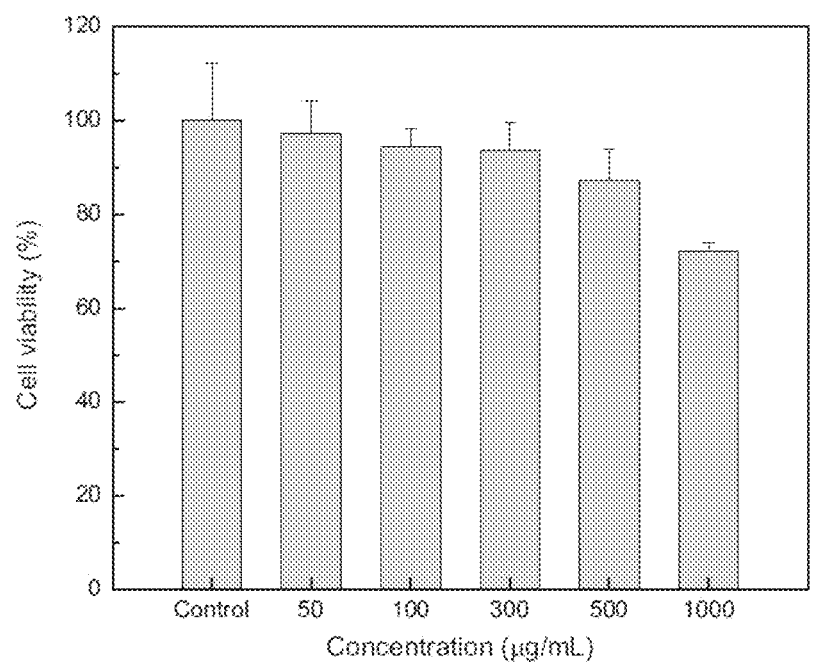
[FIG. 10]

[FIG. 11]
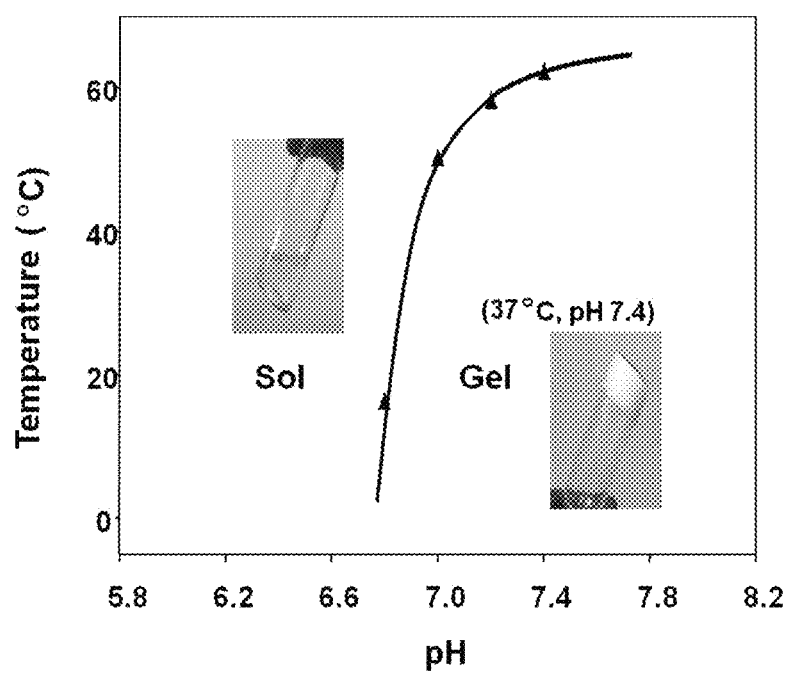

[FIG. 12]
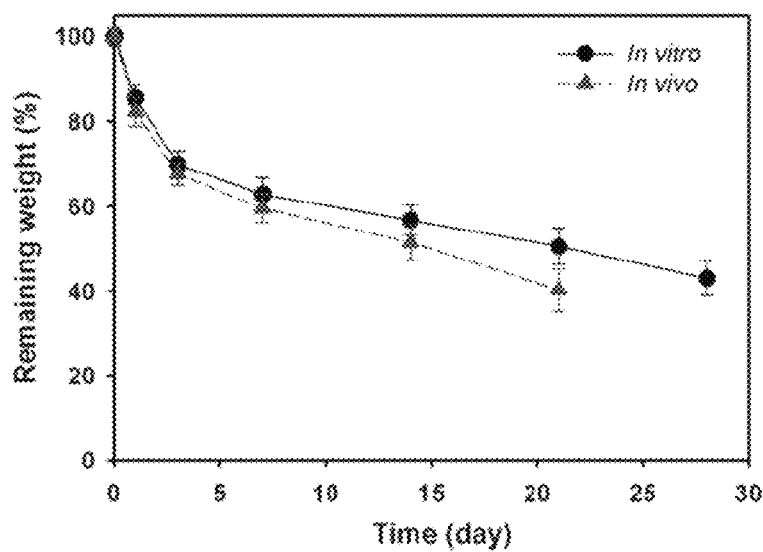

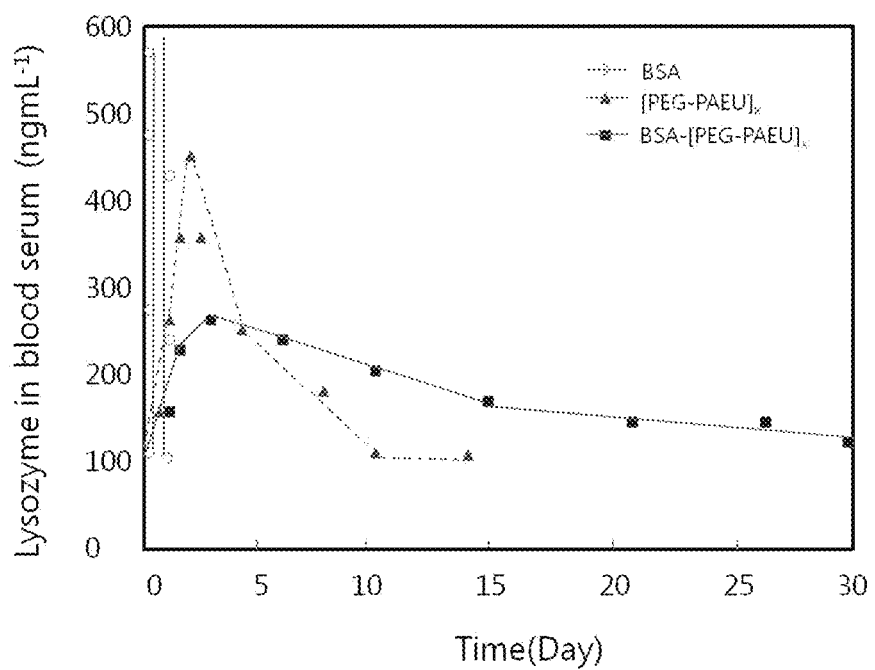
[FIG. 13]

US 9,782,486 B2

ALBUMIN CONJUGATED TEMPERATURE AND PH-SENSITIVE MULTI-BLOCK COPOLYMER, A METHOD OF PREPARATION THEREOF AND DRUG DELIVERY SYSTEM USING THE SAME

CROSS-REFERENCE TO RELATED APPLICATIONS

This application claims the benefit priority under 35 U.S.C. §119(e), of Korean Patent Application No. 10-2014-0095998 filed on Jul. 28, 2014, in the Korean Intellectual Property Office. The entire disclosure of which is incorporated herein by reference for purposes.

TECHNICAL FIELD

The present invention relates to a conjugate of albumin and a temperature- and pH-sensitive multi-block copolymer, a method of preparation thereof, and a sustained-release drug carrier comprising the same, and more specifically, to a conjugate in which polyethylene glycol-poly(amino urethane) (PEG-PAU) or polyethylene glycol-poly(amino ester urethane) (PEG-PAEU) multi-block copolymer is conjugated to albumin, a method of preparing the same, and a long-term sustained-release drug carrier comprising the same, capable of reducing an initial burst release of drugs and improving an affinity to drugs.

BACKGROUND ART

Generally, biocompatible polymers are used in performing various medical practices including diagnoses and treatments or in replacing body parts. Recently, studies have been actively performed on development of polymeric drug carriers having a regulated sol-gel transition by modifying a molecular structure of the constituent polymer to form a biodegradable polymer or an amphiphilic polymer having both a hydrophobic group and a hydrophilic group, or by forming a hydrogel using a block copolymer.

U.S. Pat. No. 5,476,909 discloses an A-B-A type triblock copolymer, wherein the hydrophobic block (A) is defiled as polylactide (PLA), polyglycolide (PGA), and copolymers thereof, and the hydrophilic block (B) is defined as polyethylene glycol (PEG) and derivatives thereof.

Additionally, U.S. Pat. No. 6,004,573 discloses an amphiphilic block copolymer useful as a drug carrier, which is a biodegradable and low molecular weight triblock copolymer comprising a hydrophobic block consisting of a polylactide (PLA)-polyglycolide (PGA) copolymer and a hydrophilic block consisting of polyethylene glycol (PEG). This triblock copolymer has an increased hydrophobic contents, and thus exists as a clear solution of sol at about from 5° C. to 25° C. and when administered into a human body, is spontaneously transformed into a gel, i.e., a water-containing semisolid at the body temperature (37° C.) with retaining the insoluble gel form in the body, and can slowly release the drug in the gel by a reverse thermal gelation.

However, the technologies described above have problems that the drug-loaded hydrogel, although sufficiently injected into a human body, can be detached from tissues due to its insufficient bioadhesiveness, or may undergo a biodegradation to cause an initial burst release phenomenon, thereby resulting in uncontrolled drug release over a long period of time.

Meanwhile, Korean Patent No. 665672 discloses a method of preparing a block copolymer hydrogel using poly(β-aminoester) as a pH-sensitive component. The temperature- and pH-sensitive block copolymer as prepared by the disclosed method is gelated at a pH ranging from 7.0 to 7.4, which is similar to that in the body and is isolated at a lower pH range, hence safely forming gel in the body without clogging an injection needle, shown by the conventional temperature-sensitive hydrogel on human injection. As such, the prepared block copolymer can be applied to a targeted drug delivery carrier capable of responding to a specific temperature and pH for from one week to two weeks.

However, the above-described hydrogel has problems that its main chain consists of an ester bond and an amide bond, both of which are biodegradable, thus rather sharply decreasing the gel strength at the early stage of human injection, and that it requires a complicated multi-step reaction to induce a urethane reaction with a starting material of polyurethane after reacting polyethylene glycol with the biodegradable polymers, and separation and purification of unreacted materials.

The present inventors, while working on the temperature- and pH-sensitive biocompatible polymers with a long-term sustained-release drug release profile, succeeded in synthesizing a hydrophilic and temperature-sensitive polyethylene glycol-poly(amino urethane urea) multi-block copolymer, and also confirmed that it has a long-term sustained-release drug release profile and the temperature- and pH-sensitive properties, and filed Korean Patent Application No. 10-2012-0071412 based on the same.

Under the circumstances, the present inventors, while endeavoring to find a method to further reduce the drug release rate of the temperature- and pH-sensitive multi-block copolymer, discovered that a conjugate of albumin and polyethylene glycol-poly(amino urethane) (PEG-PAL) or polyethylene glycol-poly(amino ester urethane) (PEG-PAEU) multiblock copolymer can significantly reduce the initial burst release of the drug, and also can further reduce the drug release rate to enable a long-term drug delivery, and completed the present invention.

SUMMARY OF THE INVENTION

An objective of the present invention is to provide a conjugate, in which a multi-block copolymer is conjugated to albumin, which can reduce the initial burst release of a drug and further reduce the drug release rate thereby enabling a long-term drug release.

Another objective of the present invention is to provide a method for preparing a conjugate, which is formed by conjugation of the multi-block copolymer to albumin.

A further objective of the present invention is to provide a long-term sustained-release drug carrier capable of reducing the initial burst drug release comprising the conjugate of the multi-block copolymer conjugated to albumin.

In order to accomplish the above objectives, the present invention provides a conjugate of albumin and a multi-block copolymer, wherein the multi-block copolymer is conjugated to the albumin, and the multi-block copolymer has a number average molecular weight from 10,000 g/mol to 25,000 g/mol and has repeating units of Chemical Formula 1:

[Chemical Formula 1]

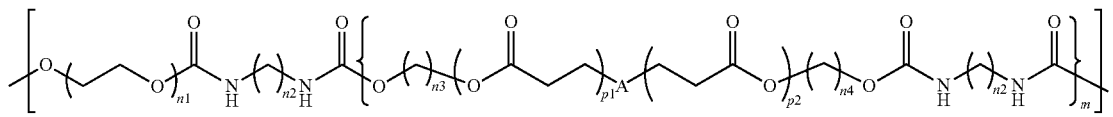

wherein, in the above formula,
A is

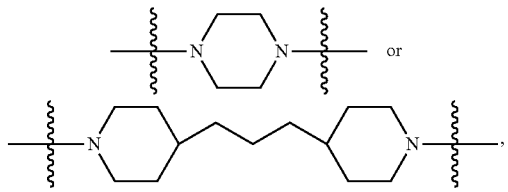

n1 is an integer from 5 to 50,
n2 is an integer from 2 to 8,
n3 is an integer from 1 to 10,
n4 is an integer from 1 to 10,
p1 is 0 or 1,
p2 is 0 or 1, and
m is an integer from 2 to 6.

Additionally, n2 is preferably 6, and n3 is preferably 2.

Preferably, the molecular weight of the multi-block copolymer is in the range from 10,000 g/mol to 25,000 g/mol. When the molecular weight of the multi-block copolymer is less than 10,000 g/mol, the sol-gel transition behavior by the change in temperature and pH does not appear under the human physiology condition. When the molecular weight of the multi-block copolymer is greater than 25,000 g/mol, neither does the sol-gel transition behavior under the human physiology condition.

Additionally, the multi-block copolymer preferably has a molecular weight ratio between the hydrophilic block and the hydrophobic block in the range from 1:2 to 1:4. The n1 block always acts as a hydrophilic block, and the n2 block always acts as a hydrophobic block, whereas n3 block acts as a hydrophilic block in an ionized state, and it acts as a hydrophobic block in a non-ionized state.

In the present invention, the multi-block copolymer represented by Chemical Formula 1 may be polyethylene glycol-poly(amino urethane) (PEG-PAU) multi-block copolymer or polyethylene glycol-poly(amino ester urethane) (PEG-PAEU) multi-block copolymer, depending on values of p1 and p2. That is, when p1 and p2 are 0, the multi-block copolymer represented by Chemical Formula 1 is the PEG-PAU multi-block copolymer, whereas when p1 and/or p2 are 1, the multi-block copolymer represented by Chemical Formula 1 is the PEG-PAEU multi-block copolymer.

In the present invention, the p block of the multi-block copolymer, being an ester moiety, acts as a hydrophilic block, and because it can be degraded in vivo, it may serve to regulate to shorten the release time of a given drug. In the present invention, the PEG-PAU multi-block copolymer may have a drug release time of more than a month. However, the PEG-PAEU multi-block copolymer may have a drug release time of two to three weeks because the ester moiety in the p block can be decomposed in vivo.

In the present invention, the conjugation between the multi-block copolymer and albumin may be achieved via an acryloyl group as a linker, but is not limited thereto. Specifically, the albumin is conjugated to the multi-block copolymer via a linker of Chemical Formula 5 below:

[Chemical Formula 5]

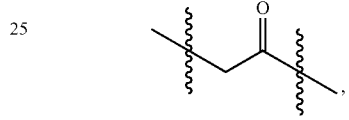

wherein the linker is formed by introducing acryloyl groups to the multi-block copolymer to attach carbonyl moieties of the acryloyl groups at polyethylene glycol block ends of the copolymer; reducing the albumin to form thiol groups at the surface thereof; and reacting vinyl moieties of the acryloyl groups with thiol groups on the surface of the reduced albumin to form a single bond.

In the present invention, a molar ratio of the multi-block copolymer to albumin cysteines is preferably in the range from 1:1 to 1:10. In the molar ratio of the multi-block copolymer to albumin cysteines, if the cysteine content in albumin is less than 1 mole relative to 1 mole of the multi-block copolymer, an excess of the multi-block copolymers remains, whereas if the cysteine content in albumin is more than 10 moles relative to 1 mole of the multi-block copolymer, it may be difficult to form a hydrogel.

Additionally, the present invention also provides a method for preparing the above conjugate, comprising:

preparing a multi-block copolymer, which has a number average molecular weight from 10,000 g/mol to 25,000 g/mol and has a repeating unit of Chemical Formula 1, by reacting a compound of Chemical Formula 2 below, a compound of Chemical Formula 3 below, and a compound of Chemical Formula 4 below (step 1);

preparing an acrylated multi-block copolymer by reacting the multi-block copolymer with acryloyl halide (step 2); and reacting albumin with a thiol reducing agent and then reacting the reduced albumin with the acrylated multi-block copolymer (step 3):

[Chemical Formula 1]

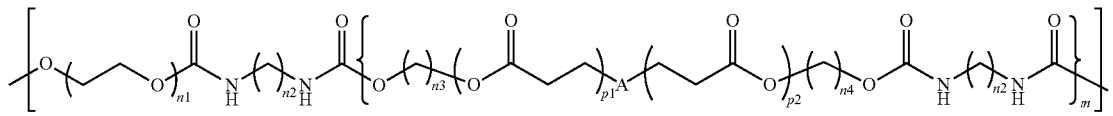

[Chemical Formula 2]

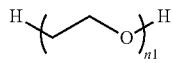

[Chemical Formula 3]

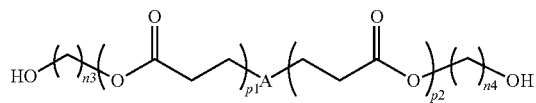

[Chemical Formula 4]

wherein, in the above formulas,
A is

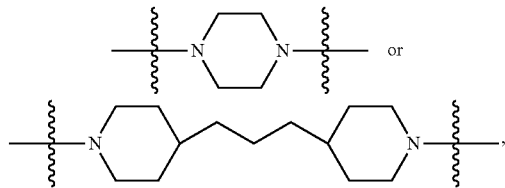

n1 is an integer from 5 to 50,
n2 is an integer from 2 to 8,
n3 is an integer from 1 to 10,
n4 is an integer from 1 to 10,
p1 is 0 or 1,
p2 is 0 or 1, and
m is an integer from 2 to 6.

Step 1 above relates to the preparation of a polyethylene glycol-poly(amino urethane) (PEG-PAU) or a polyethylene glycol-poly(amino ester urethane) (PEG-PAEU) multi-block copolymer, which has a number average molecular weight from 10,000 g/mol to 25,000 g/mol and includes repeating units represented by Chemical Formula 1, by reacting a compound of Chemical Formula 2, a compound of Chemical Formula 3, and a compound of Chemical Formula 4.

In the present invention, the compound represented by Chemical Formula 2, due to its hydrophilicity and temperature characteristic, may exhibit an in vivo sensitivity, and in particular, an in vivo temperature-sensitivity. Accordingly, the compound may form a hydrogel or maintain a sol state according to temperature change.

In the present invention, the compound represented by Chemical Formula 2 preferably has a number average molecular weight from 500 g/mol to 5,000 g/mol.

In the present invention, the compound represented by Chemical Formula 3, including a tertiary amine group which can be ionized at pH 7.0 or below, may exhibit in vivo pH-sensitivity. Accordingly, the compound may form a hydrogel or maintain a sol state according to pH changes.

In the present invention, preferably, the compound represented by Chemical Formula 3 is at least one selected from the group consisting of 1-(2-hydroxyethyl) piperazine (HEP), 1-(2-hydroxypropyl) piperazine (HPP), 1-(2-hydroxybutyl) piperazine (HBP), 1-(2-hydroxyhexyl) peperazine (HHP), and 4,4'-trimethylenedipiperidine (TMDP), but is not limited thereto.

In the present invention, preferably, the compound represented by Chemical Formula 4 is at least one selected from the group consisting of 1,2-ethylene diisocyanate, 1,4-tetramethylene diisocyanate, and 1,6-hexamethylene diisocyanate, but is not limited thereto.

In the present invention, preferably, the above reaction is performed in the presence of at least one catalyst selected from the group consisting of dibutyltin dilaurate, stannous octoic acid, stannous chloride, iron oxide, aluminum triisopropoxide, $CaH_2$, Zn, and lithium chloride.

In the present invention, preferably, the molar ratio among the compound represented by Chemical Formula 2, the compound represented by Chemical Formula 3, and the compound represented by Chemical Formula 4 is in the range from 1:5:10 to 1:10:15. When the molar ratio of the compound represented by Chemical Formula 3 is smaller than 5, polyruea oligomers having a hydroxyl end group are less likely to be formed. In contrast, when the molar ratio of the compound represented by Chemical Formula 3 is greater than 10, it is difficult to control the block length of the block copolymer. Additionally, when the molar ratio of the compound represented by Chemical Formula 4 is smaller than 10, poly(amino urethane) oligomers having a hydroxyl end group are less likely to be formed. In contrast, when the molar ratio of the compound represented by Chemical Formula 4 is greater than 15, it is difficult to control the block length of the block copolymer.

In the present invention, preferably, the reaction of step 1 is performed at from 40° C. to 80° C., and preferably, for from 1 hour to 3 hours.

Step 2 relates to preparing an acrylated multi-block copolymer by reacting the multi-block copolymer represented by Chemical Formula 1 with an acryloyl halide.

In the present invention, specific examples of the acryloyl halide may include an acryloyl chloride and a methacryloyl chloride, but are not limited thereto.

In the present invention, preferably, the reaction between the multi-block copolymer and the acryloyl halide is performed at a molar ratio of the hydroxyl end group of the multi-block copolymer to the acryloyl halide from 1:1 to 1:3, and most preferably 1:1.5.

In the present invention, the reaction of step 2 may be performed in the presence of triethylamine Preferably, triethylamine may be used at a molar ratio from 1:1 to 1:3 relative to the hydroxyl end group of the multi-block copolymer, and most preferably 1:1.

In the present invention, preferably, the reaction of step 2 is performed under a nitrogen or argon atmosphere.

Step 3 relates to a conjugation between albumin and the acrylated multi-block copolymer, which includes reacting albumin with a thiol reducing agent to reduce the cysteine bond (—S—S—) of albumin to a thiol (—SH) group, and then subsequently reacting the reduced albumin with the acrylated multi-block copolymer, so that the vinyl moiety of the acryloyl end of the acrylated multi-block copolymer can react with the thiol group on the surface of albumin thereby forming a single bond.

In step 3 of the present invention, preferably, the reaction molar ratio of the acrylated multi-block copolymer to albumin cysteines is in the range from 1:1 to 1:10. If the cysteine content in albumin is less than 1 mole relative to 1 mole of the multi-block copolymer, an excess of the multi-block copolymers remains, whereas if the cysteine content in albumin is more than 10 moles relative to 1 mole of the multi-block copolymer, it may be difficult to form a hydrogel.

Additionally, the present invention provides a sustained-release drug carrier comprising a conjugate of albumin and a multi-block copolymer, wherein the multi-block copolymer is conjugated to the albumin, and the multi-block copolymer has a number average molecular weight from 10,000 g/mol to 25,000 g/mol and has repeating units of Chemical Formula 1.

In the present invention, drugs that can be used in the sustained-release drug carrier may include paclitaxel, doxombicin, docetaxel, chlororambucil, insulin, exendin-4, human growth hormone (hGH), erythropoietin (EPO), granulocyte colony stimulating factor (G-CSF), granulocyte-macrophage stimulating factor (GM-CSF), lysozyme, bovine serum albumin, antimicrobial agents, steroids, anti-inflammatory analgesic agents, sex hormones, immunosuppressants, antiviral agents, anesthetic agents, antiemetics, antihistamines, etc., but are not limited thereto.

In the present invention, the tertiary amine moiety of the multi-block copolymer can be ionized at pH 7.0 or below and take a positive charge (+), while the above drugs can take negative charges (−) at pH 7.0 or below. Accordingly, the drugs can be bound to the multi-block copolymers in a sol state at pH 7.0 or below before injection, thereby forming drug carriers. Later, when the drug carriers are injected into the body, they are gelated in an in vivo environment at from pH 7.0 to pH 7.4 and the drugs are slowly released therefrom.

In the present invention, the long-term sustained-release drug carrier may be in the form of an injectable hydrogel.

Additionally, the multi-block copolymers of the present invention, being conjugated to albumin, provide a physically-crosslinked structure, wherein the drugs is more slowly released, thus assisting drug carriers to release drugs for a longer period of time while reducing the initial burst release of the drugs, compared to the multi-block copolymers not conjugated to albumin.

In the present invention, the long-term sustained-release drug carriers are characterized in that they have a sustained release profile over a period of 2 weeks to 5 weeks.

Advantageous Effects

The conjugate of the present invention is effective for a long-term sustained drug release, since the conjugate is formed by conjugating albumin to a temperature- and pH-sensitive multi-block copolymer which is prepared by mixing and reacting a compound of Chemical Formula 2 having a hydrophilicity and temperature characteristic with a compound of Chemical Formula 3 having a pH-responsive ionization characteristic, thereby significantly reducing the initial burst release of drugs and also further slowing down the drug release rate.

Additionally, since the temperature- and pH-sensitive multi-block copolymer is safe in the body, it can be applied to the fields such as medical treatments, gene transfer, and drug delivery, and in particular, it can be applied to sustained-release drug carriers for drug loading and release, and also applied to diagnostic uses such as diagnostic imaging by delivering diagnostic materials to abnormal cells.

Furthermore, the conjugate of the present invention is applicable to a cancer cell targeted drug delivery, since it forms a hydrogel at pH from 7.0 to 7.4, the same pH as in the normal body, whereas maintaining a sol state at pH 7.0 or below, an abnormal condition such as cancer cells, and in addition to the above cancer targeted delivery, it has applicability to a genetic mutations and other application fields by appropriately varying the constituting components, molar ratio, molecular weight and/or functional groups in the polymer block in preparing the conjugate of albumin and multi-block copolymer.

BRIEF DESCRIPTION OF DRAWINGS

FIG. 1 shows FT-IR spectra of BSA (a), PAU multi-block copolymer (b), and PAUBSA1 (c) and PAUBSA2 (d) as PAUBSA conjugates of Example 1.

FIG. 2 shows a sol-gel phase diagram of 25 wt % PAU solution (□), 20 wt % PAUBSA1 solution (●), 25 wt % PAUBSA1 solution (○), 20 wt % PAUBSA2 solution (▲), and 25 wt % PAUBSA2 solution (Δ).

FIG. 3 shows a graph illustrating in vitro lysozyme release behavior from PAU (■), PAUBSA1 (●), and PAUBSA2 (▲) hydrogels.

FIG. 4 shows graphs illustrating the measurement results of zeta potential according to various polymers/lysozyme ratios at pH 7.4.

FIG. 5 shows pictures illustrating in situ gelation and stability of PAUBSA1/lysozyme hydrogel in a male SD rat.

FIG. 6 shows a graph illustrating the changes in concentration of lysozyme in the blood serum of a male SD rat after treatment with a lysozyme solution (■), a PAU hydrogel loaded with lysozyme (●), and a PAUBSA1 hydrogel loaded with lysozyme (▲), respectively.

FIG. 7 shows FT-IR spectra of BSA (top), a PAU copolymer (middle), and a conjugate (bottom) in Example 2.

FIG. 8 shows a sol-gel phase diagram (a) of PAU2 and PAU2BSA, a sol-gel phase diagram (b) of PAU4 and PAU4BSA, and the representative pictures illustrating the pH and temperature-sensitive transition of a conjugate from a sol state to a gel state.

FIG. 9 shows a graph illustrating in vitro DOX release behavior from 25 wt % PAU2 and 25 wt % PAU2BSA.

FIG. 10 shows a graph illustrating in vitro cytotoxicity of PAU2BSA at varied concentrations using L929 fibroblasts.

FIG. 11 shows a sol-gel phase diagram of a PAEU conjugate in Example 3.

FIG. 12 shows a graph illustrating in vivo and in vitro gel degradation behavior of a PAEU conjugate in Example 3.

FIG. 13 shows a graph illustrating in vivo lysozyme release behavior of BSA (○), PAEU (▲) and PAEU conjugates (■) in Example 3.

DETAILED DESCRIPTION OF THE INVENTION

The present invention will be explained in greater detail through the following examples as set forth herein below, but they are disclosed for illustrative purposes only and are not to be construed as limiting the scope of the present invention.

EXAMPLE 1

Preparation of PAU-BSA Conjugates Having Various PAU Molar Ratios Relative to Albumin Cysteine Poly(ethylene glycol) (PEG, $M_n$=2000 and $M_n$=4600), bis-1,4-(hydroxylethyl)piperazine (HEP), hexamethylene diisocyanate (HDI), dibutyltin (II) dilaurate, anhydrous toluene, anhydrous N,N-dimethyl formamide (DMF), anhydrous chloroform (CHCl$_3$), phosphate buffer saline (PBS), BSA, chicken egg white lysozyme, tris(2-carboxyethyl) phosphine hydrochloride (TCEP-HCl), acryloyl chloride, and triethylamine used in the experiment were purchased from Sigma-Aldrich (St. Louis, Mo., USA), and diethyl ether, acetone and all other reagents were analytical grade.

Step 1: PAU Synthesis

PAU was synthesized using a method described in the previously reported reference (D. S. Lee et al., Polymer, 2008, 49, 4968). In brief, polycondensation was performed in a stoichiometric ratio between the OH and NCO groups, OH/NCO=1. To a 250 mL round bottom flask equipped with a magnetic stirring bar was added 1.0 mmol PEG (M$_n$=2000). To remove water from the PEG, the flask was placed into an oil bath at 100° C. under vacuum for 2 hours. After cooling to 80° C., HEP and 1 wt % dibutyltin dilaurate in CHCl$_3$ were put in the flask, and the vacuum was reapplied for additional 30 minutes. Then, 60 mL of anhydrous toluene/DMF (50:50) was added as a solvent, and the resulting mixture was stirred until HEP was completely dissolved. The resultant was added with a predetermined amount of HDI, and allowed to react at 80° C. In 2 hours, the solvent was removed by evaporation, and the resulting product was dissolved again in CHCl$_3$. The resultant was precipitated in a 10-fold excess of ice-cold diethyl ether to obtain PAU, filtered and repeatedly washed with diethyl ether, and finally dried in a vacuum oven for at least 48 hours.

Step 2: Preparation of Acrylated PAU

Acrylated PAU (APAU) was prepared from the PAU synthesized in Step 1 above as described below.

In brief, PAU was acrylated under argon atmosphere by reaction with acryloyl chloride and triethylamine, at a mole ratio of 1.5:1 relative to the OH group. The resulting product was precipitated in an ice-cold diethyl ether and dried in a vacuum oven for at least 48 hours. By using proton NMR ($^1$H NMR), the end group conversion (>90%) and the purity of the final product (data not shown) was confirmed.

Step 3: Synthesis of PAU-BSA Conjugate

The conjugation between PAU and BSA was performed by modifying a method described in the previously reported reference (L. Oss-Ronen, D. Seliktar, Acta Biomater. 2011, 7, 163) in Reaction Scheme 1 as shown below:

[Reaction Scheme 1]

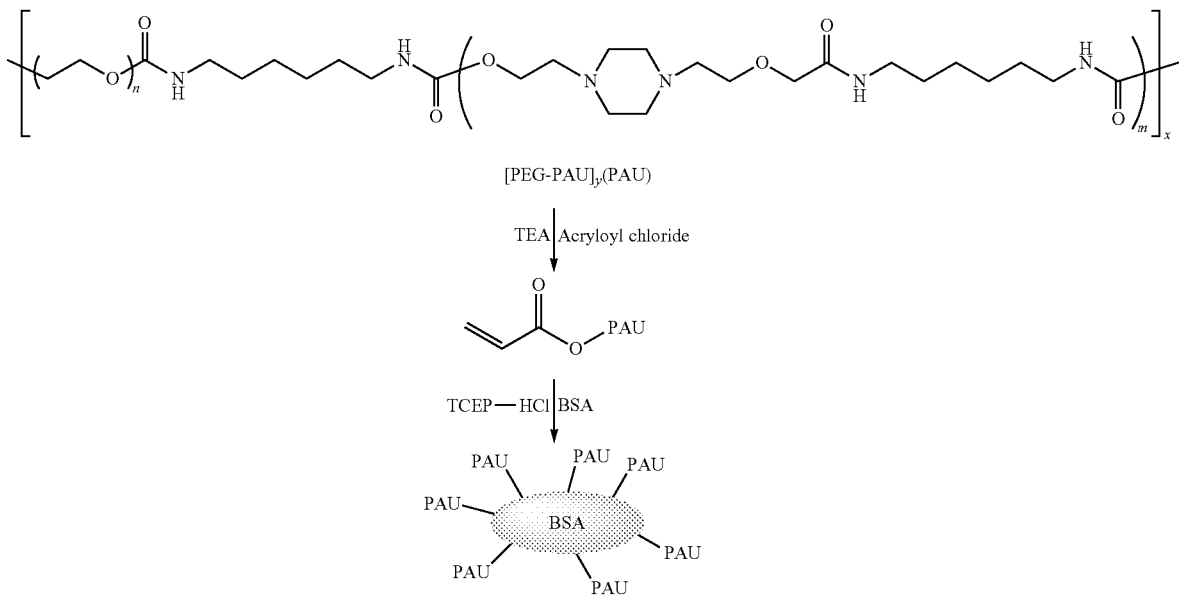

As shown in Reaction Scheme 1, TCEP-HCl was added to 7 mg/mL BSA (the molar ratio of TCEP:albumin cysteines was 2:1) solution in PBS containing 8 M urea. Then, APAU was added to the BSA solution and allowed to react at room temperature overnight (the molar ratio of APAU:albumin cysteines was 1:1). The reactants were precipitated in acetone, redissolved in PBS containing 8 M urea, dialyzed against PBS (12-14 kDa MW cut-off, Spectrum, Gardena, Calif.) at 4° C. for two days, lyophilized to obtain a conjugate (PAUBSA1) before its later use. Then, a conjugate (PAUBSA2) having 1:2 molar ratio of APAU to albumin cysteines was synthesized by a similar process. The details of the synthesis are summarized in Table 1 below.

TABLE 1

| Samples | PAU feed | | | | | | PAUBSA feed ratio [mol] | |
|---|---|---|---|---|---|---|---|---|
| | PEG | ratio [mol] | | | PAU | | | BSA |
| | $\overline{M}_n{}^{a)}$ | PEG | HEP | HDI | $\overline{M}_n{}^{b)}$ | PDI$^{b)}$ | PAU | cysteine |
| PAU | 2000 | 1 | 10 | 11 | 7254 | 1.26 | — | — |
| PAUBSA1 | | | | | | | 1 | 1 |
| PAUBSA2 | | | | | | | 1 | 2 |

$^{a)}$Provided by Sigma-Aldrich;
$^{b)}$obtained by GPC

Experimental Example 1

Analysis of Characteristics of Conjugates of the Present Invention

The characteristics of PAU-BSA conjugate prepared in Example 1 were analyzed as described below.

1) Characterization by FT-IR and SDS-PAGE

In order to confirm the introduction of functional groups in the multi-block copolymers prepared in Example 1 and the reactions of their end groups, FT-IR measurement was performed. FT-IR spectra were obtained via an FT-IR spectrometer (FT/IR-4100 Type A, TGS, Jasco). Additionally, the native BSA and the conjugates were loaded onto an 8% polyacrylamide gel (5-10 μg of samples per each lane) and the presence of the conjugated products between PAU and BSA, i.e., the production of a conjugate, were confirmed by SDS-PAGE. The gel was stained with Coomassie blue and digitally imaged.

In Example 1, the multiblock copolymers were synthesized using PEG, HDI, and HEP as monomers. PAU was acrylated by reacting with acryloyl chloride before being conjugated to BSA. The conversion rate of PAU into the acrylated PAU was 95% or higher. The PAU-BSA conjugation was accomplished by Michael addition reaction between the vinyl group of the acrylated PAU and the thiol group of BSA. The FT-IR spectra of BSA (a), PAU multi-block copolymer (b), and PAUBSA1 (c) and PAUBSA2 (d), as PAUBSA conjugates, are shown in FIGS. 1a to 1d.

Compared with the spectra of the native BSA and PAU, the spectra of the PAUBSA conjugates (both PAUBSA1 and PAUBSA2) exhibited the characteristic bands of both BSA and PAU (FIGS. 1a to 1d). That is, in addition to the noticeable N—H stretching vibration at 3421 cm$^{-1}$, an amide band representing different vibrations of the peptide moiety was distinctively shown in the conjugate. The amide I band (#1, absorption associated with a C=O stretching mode) and the amide II band (#2, absorption associated with a C—N stretching mode and a N—H bending mode) appeared at 1600-1700 cm$^{-1}$ and 1533 cm$^{-1}$, respectively. The two vibrations are typical bands widely used for protein characterization Regarding the PAU part, the ether band of PEG (#4, absorption associated with a C—O—C stretching mode) was observed at 1101 cm$^{-1}$, and the band (#3) corresponding to C—N stretching of HEP aromatic group appeared at 1259 cm$^{-1}$. The bands that appeared on the FT-IR spectra of the conjugates confirmed that the conjugations between the multi-block copolymers and BSA were successfully achieved.

Additionally, the conjugations between the multi-block copolymers and BSA in the above conjugate were confirmed via SDS-PAGE as shown in FIG. 1e.

BSA, PAUBSA1 and PAUBSA2 were loaded onto an 8% polyacrylamide gel and compared using a molecular marker, and as a result, an increase in their molecular weight and polydispersity were observed. The molecular weight of PAUBSA1 and PAUBSA2 was in the range from 100 kDa to 250 kDa, and from 50 kDa to 250 kDa, respectively. The mobility of the conjugates (PAUBSA1 and PAUBSA2 in lane B and lane C, respectively) was significantly reduced compared to that of the native BSA (lane A). When the PAU/cysteine ratio was 1:1 (PAUBSA1), BSA was completely conjugated to the copolymers, and when the cysteine concentration increased (PAUBSA2) in the reaction, the residue of BSA was observed.

2) Sol-Gel Phase Transition Behavior According to pH and Temperature

The sol-gel phase transition behavior of PAU and PAUBSA conjugates in an aqueous solution was measured by the test tube inverting method.

First, each sample was dissolved in PBS at pH 4 within a 5 mL vial tube at a predetermined concentration, and the sol-gel phase transition behavior according to pH was measured while adjusting pH of the solution to a desirable pH using NaOH and HCl. The sol-gel transition was confirmed by observing that the sample did not flow when the vial was turned upside down.

Additionally, the sol-gel phase transition behavior according to temperature was measured by a method which includes placing a vial containing about 0.5 mL of a solution into a temperature-controlled water bath, being heated at temperature intervals of 2° C., and maintaining equilibrium for 10 minutes. The sol-gel transition was confirmed by observing that the sample did not flow when the vial was turned upside down.

The sol-gel phase diagrams of the PAU, and PAUBSA1 and PAUBSA2 conjugates are shown in FIG. 2.

As shown in FIG. 2, the PAU multi-block copolymer having pH 6.8 was observed to undergo a transition from sol to gel at 40° C., and the gelation temperature was reduced as pH of the solution increased. Gel formation was regarded to occur via interconnection of polymeric micelles. Micelles consisting of a HEP-HDI hydrophobic core and a PEG hydrophilic shell are formed within the solution. The system remained in a sol state due to the PEG's hydrophilicity at low temperature and the HEP's ionization at low pH, rendering the complete solubility of the whole system in the aqueous solution. When increasing pH, HEP was progressively deionized and became more hydrophobic. Additionally, PEG started to be dehydrated when increasing temperature. Due to the dehydration property of PEG and hydrophobicity of HDI, the hydrophobic interaction in the HEP-HDI overcame the hydrophilic interaction between water and PEG segments, and as a result, the copolymer solution was gelated at the transition temperature and pH. A hydrogel administration requires a complete transition at physiological conditions, i.e., at pH 7.4 and 37° C., and stability of the hydrogel. The solution was gelated at 32° C. when the pH value was 7.4, which literally made the body condition located too close to the phase boundary. The gelation was not observed below 32° C. at all pH values because hydrophilicity was dominated at these conditions. Additionally, the phase transition from gel to sol appeared at 84° C. at all pH values. The complete dehydration of PEG attributed to the appearance of the upper phase boundary.

The phase diagrams of the conjugates (both PAUBSA1 and PAUBSA2) exhibited stronger hydrophobicities than the PAU hydrogel having a similar concentration (25 wt %). The gel window well covered the physiological conditions, and accordingly, the solution was completely converted to a stable gel under the physiological conditions. When being conjugated to BSA, the sol-gel transition of PAUBSA1 and PAUBSA2 moved to a lower temperature due to the addition of the protein. The acrylation of PAU can generate diacrylated copolymers having a reactive vinyl group at both ends of the copolymer chains. In other words, a network covalently bound between the diacrylated PAUs and several thiol groups within BSA may be formed. The crosslinked network was thought to cause a drastic increase of molecular weight and an increase of hydrophobicity, thereby lowering the sol to gel transition temperature of conjugates at all pH values.

Additionally, the effect of concentration on the sol-gel diagram was examined over the conjugate solution. As the solution concentration decreased from 25 wt % to 20 wt %, the sol-gel transition moved to a higher temperature at all pH values. Due to the relatively low hydrophobic density of the 20 wt % solution, the system required a sufficient hydrophobic interaction for the gelation of the network, which can be achieved by increasing temperature. Additionally, the upper phase boundary did not appear on the conjugate hydrogels.

Additionally, in order to investigate the effect of albumin composition on the sol-gel phase transition, the phase diagrams of PAUBSA1 and PAUBSA2 were compared at the same concentration range. FIG. 2 shows that the phase diagram of PAUBSA2 was positioned below the phase diagram of PAUBSA1 at the respective concentrations. The result indicates that the sol-gel transition temperature was lowered by increasing the molar ratio of BSA in the hydrogel. FIG. 2 also showed the inset pictures that represented the flowing liquid and the solid gel in the sol state and in the gel state, respectively.

As shown in Table 1 above, the molecular weight of the PAU (Mn=7250) used in the preparation of conjugates of the present invention was significantly lower than the PAU (Mn=30000) synthesized previously by Dayananda (K. Dayananda et al., Polymer, 2008, 49, 4968). However, the sol-gel phase diagrams of the two PAU systems were similar. The analysis of urine excretion showed that PEG-based polymers having a particular molecular weight range (MW<20000) were excreted within 24 hours (R. B. Greenwald et al., Adv. Drug Delivery Rev., 2003, 55, 217). According to the enzymatic digestion of BSA, the PAU with a relatively low molecular weight should benefit the suitability for renal clearance after degradation of hydrogels.

3) In Vitro Release

Each of the sample solutions having a 25 wt % concentration was mixed with lysozyme having a 10 mg/mL concentration. 0.5 g of each sample was put into a vial, and was gelated by adjusting its pH to 7.4 in a water bath set at 37° C. As a release medium, 5 mL of PBS containing 0.02 wt % $NaN_3$ was added into the vial containing a hydrogel. At predetermined time intervals, 2 mL of the release medium was removed for measurement, while 2 mL of a fresh buffer was replaced in the same vial. The lysozyme release was measured via a BCA assay. Additionally, the hydrogels without lysozyme were measured as background, and the values were subtracted from those of the lysozyme-loaded hydrogels to measure the actual amount of the lysozyme released.

The in vitro release test was performed in order to compare release behavior of the protein-loaded hydrogel. Lysozyme was loaded into the different hydrogel matrices and the results are shown in FIG. 3. A burst effect appeared during the initial stage of the lysozyme release from the PAU hydrogel, and the amount of the lysozyme release reached the threshold (almost 80%) approximately in two weeks. Meanwhile, the conjugate hydrogel exhibited a significant decrease in the burst effect during the initial release period. The release of lysozyme from PAUBSA1 and PAUBSA2 proceeded with a more sustained release pattern than that of the PAU hydrogel. Such conjugate hydrogels maintained these behaviors, as the lysozyme being released, for more than four weeks, with the contents achieving 60% and 40% for lysozyme being released from the PAUBSA1 and PAUBSA2, respectively. The relatively slow release of lysozyme from the conjugate hydrogels may be attributed to the binding affinity of BSA for certain drugs and proteins, which lead to unusual retardation of the entrapped molecules being released from the matrices. The result was verified by comparing the release of lysozyme from the conjugate hydrogels consisting of various BSA compositions. The release of lysozyme from PAUBSA2 was much slower than that from PAUBSA1, BSA content of which was a half of that of the PAUBSA2. With increasing BSA composition, the entrapped molecules were able to get accessed to more affinity sites, and were well retained within PAUBSA2 accordingly. Due to the excellent sustainability with a sufficient release amount of lysozyme (>50% within 3 weeks), PAUBSA1 was selected for a further in vivo experiment.

Lysozyme was used as a model protein because its structure and properties, including solution behavior, have been well-characterized. Lysozyme maintained its thermal stability up to 72° C. in the presence of an anionic modified polymer, suggesting that the secondary structures of lysozyme were preserved below the above temperature. Additionally, the lysozyme activity was maintained over a wide pH range (6.0~9.0). Additionally, the previous studies on lysozyme released from PEG-based hydrogels and other polymeric devices showed that its activity maintained to the degree of about 95% of bioactivity up to 28 days, and even 100% of bioactivity up to 50 days. Based on these previous studies, the bioactivity of the lysozyme released from the hydrogels of the present invention appeared to be retained or, in the worst case, may have been lost in part during the experiment.

4) Measurement of Zeta Potential

The zeta potential values of the PAU and PAUBSA conjugates were measured at room temperature by Metasizer Nano ZS instrument (Malvern Instrument). The solution concentrations for all samples were 1 mg/mL and their pH was adjusted to 7.4. The solutions were stabilized at room temperature for 20 minutes before measurement.

The complexations between the entrapped proteins and hydrogels were determined by monitoring the zeta potential of the samples. The zeta potential of the lysozyme solution alone was 11.2 mV, indicating the cationic property of lysozyme in a physiological pH. As shown in FIG. 4a, in the presence of a small amount of PAU, zeta potential was slightly dropped but the zeta potential increased as the PAU ratio in the solution increased. Because PAU and lysozyme are cationic molecules and weakly form a positive charge at pH 7.4 (i.e., subsequently because a polymer can trap lysozyme without any special ionic attraction) the positive values for all PAU/lysozyme preparations implied the absence of any ionic conjugate. Accordingly, the lysozyme release was accelerated by the electrostatic repulsion force between lysozyme and hydrogel matrices. Meanwhile, in the presence of a small amount of PAUBSA1, there was apparently a drastic decrease in zeta potential, whereas as the PAUBSA1 ratio in the solution increased the zeta potential decreased and became a considerably negative value. Because PAUBSA1 was the anionically modified hydrogel, and the interaction between lysozyme and BSA was rather attractive, the loaded lysozyme was immobilized by the predominated negative chares from BSA moieties, thereby providing the release in a relatively slow kinetics.

5) In Vivo Gel Formation

The 25 wt % PAUBSA conjugate solutions were subcutaneously injected on the back of a male Sprague-Dawley (SD) rat to evaluate the injectability and the in vivo gelation. At the predetermined time, the rats were sacrificed and the in situ gelation was observed by the naked eye. The result is shown in FIG. 5. The concentration of the PAUBSA1 solution was 25 wt %, and the concentration of the loaded lysozyme was 10 mg/mL. After a single subcutaneous injection, the PAUBSA1 solution instantly formed a solid gel under the rat skin within 30 minutes. The shape of the gel was stably maintained for at least three weeks, and its size became smaller due to the degradation of the copolymer as observed through its physical appearance.

6) In Vivo Release

In order to examine the in vivo release of lysozyme, a sample solution loaded with 250 μL of lysozyme was injected to male SD rats (three rats per group). At predetermined times, blood samples were collected from the caudal vein, centrifuged to obtain blood sera, and stored them at −21° C. until the next analysis. The concentration of the lysozyme in the blood sera was measured using a commercial lysozyme (LZM) ELISA kit (Cusabio, China).

FIG. 6 shows an in vivo release of lysozyme in male SD rats after a single subcutaneous injection of a lysozyme-loaded sample. Each sample contained 10 mg/mL of lysozyme in the preparation. As expected, the initial burst was obviously observed in the rat injected with the lysozyme solution. The level of lysozyme within the blood plasma reached about 447 ng/mL within two days after the injection and, then, started to decrease thereafter, and dropped to the normal level within nine days. The PAU hydrogel showed a slight decrease in the initial burst release effect of drugs, and showed a peak at 297 ng/mL. However, there was no distinct difference in release kinetics between the injected lysozymes whether the lysozyme was injected as a solution or as a lysozyme-loaded PAU hydrogel. The both of the carriers maintained the lysozyme release less than nine days before the lysozyme in blood serum dropped to the normal level. In contrast, the PAUBSA1 hydrogel not only reduced the initial burst effect, with the peak at 270 ng/mL, but also sustained the lysozyme release for two weeks or more until the concentration of lysozyme in blood serum finally reached the normal level.

EXAMPLE 2

Preparation of PAU-BSA Conjugates Using PEGs with Different Molecular Weights

All reagents were purchased from Sigma Aldrich and used without further purification PEGs with molecular weight of 2000 or 4600 were used for PAU synthesis, and were named as PAU2 and PAU4, respectively. The synthesis and acrylation of PAU were performed based on the methods described in Example 1 above. $^1$H-NMR was employed to validate the end group conversion and to verify the purity of the final products.

The conjugation between PAU and BSA was performed as shown in Reaction Scheme 2 below by modifying the method described in a previously reported reference (L. Oss-Ronen, D. Seliktar, *Acta Biomater.* 2011, 7, 163).

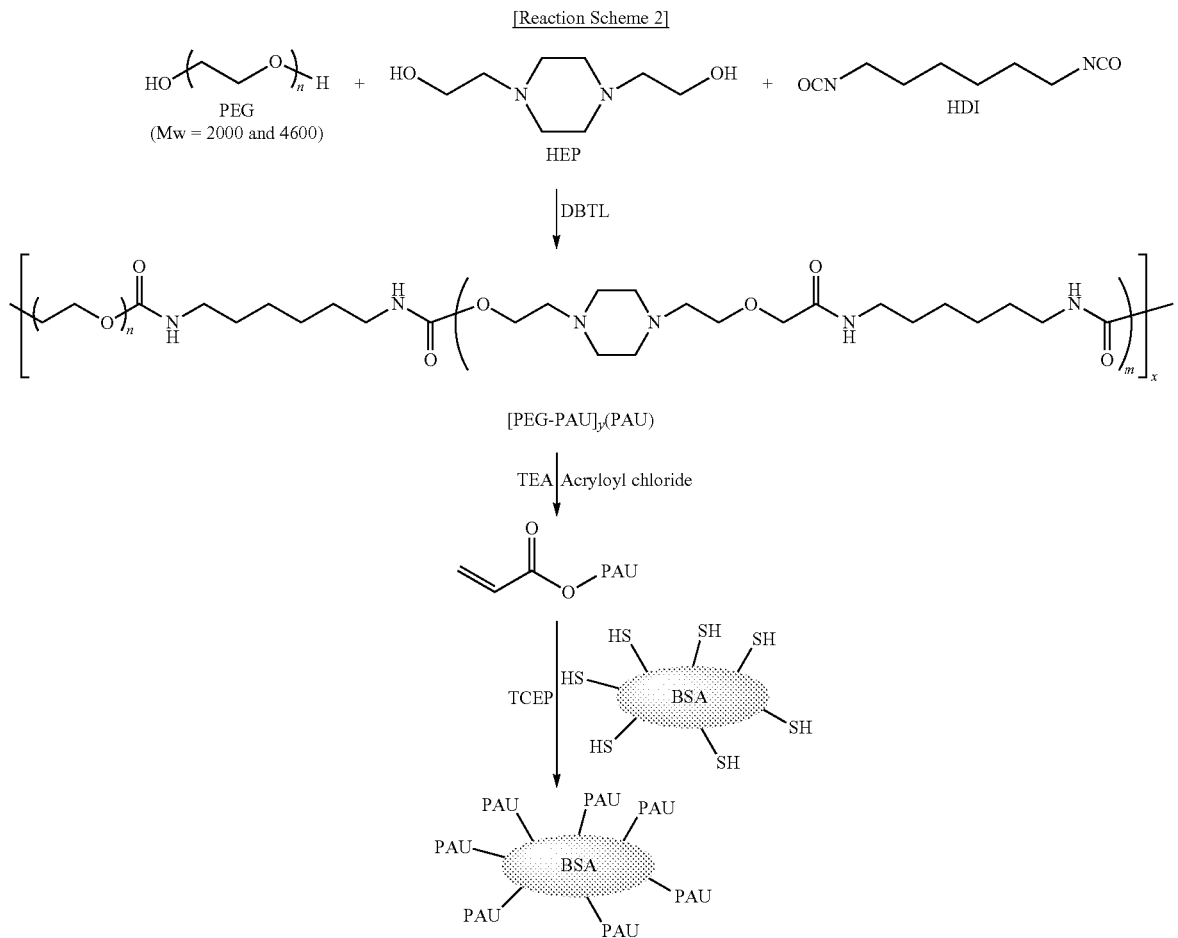

As shown in Reaction Scheme 2 above, a copolymer solution (the molar ratio of PAU:albumin cyseines was 1:1) was added to a 7 mg/mL BSA solution in 8 M urea, and was allowed to react at room temperature overnight. The reactants were precipitated in acetone, redissolved in PBS containing 8 M urea, dialyzed against PBS (12-14 kDa MW cut-off, Spectrum, Gardena, Calif.) at 4° C. for two days, lyophilized to obtain a conjugate before its later use.

Experimental Example 2

Analysis of Characteristics of Conjugates of the Present Invention

The characteristics of PAU-BSA conjugates prepared in Example 2 were analyzed as follows.

1) Characterization by FT-IR and SDS-PAGE

The copolymers and the conjugates were characterized by FT-IR.

As shown in FIG. 7, the characteristics of the conjugates were analyzed via FT-IR spectrum. The spectrum for the native BSA molecule (upper, left and right) exhibited a noticeable absorption corresponding to the N—H stretching vibration at 3421 $cm^{-1}$. The absorption bands shown at 1656 $cm^{-1}$ and 1533 $cm^{-1}$, i.e., amide I (AI, a C=O stretching vibration) and amide II (AII, a C—N stretching vibration and an N—H bending vibration) bands are typically recognized as characteristic bands for protein characterization. The spectrum of the copolymers (middle, left: PAU2 and right: PAU4) both exhibited absorptions at 3338 $cm^{-1}$, 1695 $cm^{-1}$, 1265 $cm^{-1}$, and 1101 $cm^{-1}$, which respectively expressed the N—H stretching of HEP, the C=O stretching of urethane, the C—N stretching of HEP aromatic, and the C—O—C stretching of PEG. Because the PAU4 was synthesized from the PEG with a relatively higher molecular weight, the band at 1101 $cm^{-1}$ intuitively exhibited a stronger absorption. All the characteristic bands corresponding to BSA (AI and AII) and PAU (PI and PII) appeared on the spectra of the conjugates (bottom, left: PAU2BSA and right: PAU4BSA). The conjugation was also confirmed by SDS-PAGE, in addition to the FT-IR results. As a result, the successful conjugation between the copolymers and BSA was confirmed.

2) Sol-gel Phase Transition Behavior According to pH and Temperature

The sol-gel phase transition of the copolymers (PAU2 and PAU4) and the conjugates (PAU2BSA and PAU4BSA) in an aqueous solution was confirmed by the test tube inverting method.

The gelation of copolymers occurs by the mutual connections between micelles formed by triggering the stimulus responsive polymer networks, and thus the sol-gel phase diagram may be manipulated by varying the pH and temperature of the solution.

FIG. 8 shows that the transition temperature of the PAU2 from sol to gel was 40° C. at pH 6.8, but it was lowered to 36° C. and 32° C. at pH 7.08 and pH 7.40, respectively. PAU2 exhibited an upper phase boundary which changed from a hard gel to a fluidized liquid at 76° C. at all pH values. PAU4 also exhibited a similar sol-gel phase diagram, but showed a significantly higher transition temperature (i.e., the transition temperature at pH 6.68, 7.12, 7.43, and 7.58 was 68, 52, 40, and 36° C., respectively). It was speculated that micelles with a larger size formed by a much longer PEG chain broadened the phase diagrams and caused the relatively high upper phase boundaries.

In the present invention, the sol-gel transition temperature of the copolymers was lowered upon addition of proteins. In particular, PAU2 and PAU4 may be influenced by the size increase of micelles after the formation of the conjugates. When the copolymers were conjugated to proteins, the phase diagram moved to a lower temperature at all pH values. PAU4BSA was present in a sol state at a temperature of 20° C. or below and all pH values. The solution started to become gelated starting from 24° C. at pH 7.48, and the transition temperature increased when the pH of the solution became more acidic.

PAU2BSA exhibited a similar phase behavior but it started to become gelated from 4° C. at pH 7.48, which was much lower than the transition temperature of PAU4BSA at the same pH. The sol-gel transition behaved in the same manner as the transition temperature increased when the pH of a solution became more acidic. After the formation of the conjugates, both PAU2BSA and PAU4BSA showed relatively broader phase diagrams and the upper phase boundaries disappeared. Additionally, the gel window well covered the physiological conditions (37° C. and pH 7.4) and thus the conjugate hydrogels can be useful for bioapplications. The images of conjugates in the sol state (or liquid state) and the gel state were shown in FIG. 8(c).

3) In Vitro Release of DOX

Each of the PAU2 and PAU2BSA solutions having a 25 wt % concentration was mixed with DOX to a final concentration of 500 µg/mL concentration. Each sample in the amount of 0.5 g was added into a vial, and was gelated by adjusting pH to 7.4 in a water bath set at 37° C. As a release medium, 5 mL of PBS containing 0.02 wt % $NaN_3$ was added into the vial. At predetermined time intervals, 2 mL of the release medium was removed for measurement, and 2 mL of a fresh buffer was replaced in the same vial. The DOX release was analyzed by a UV-VIS spectrometer set at 495 nm.

As illustrated in FIGS. 8(a) and 8(b), both PAU2BSA and PAU4BSA can be injected but the proper gelation (i.e., the gel window should well cover the physiological conditions) is more essential. Accordingly, a PAU2BSA-based conjugate hydrogel was selected, and confirmed that such a system can potentially load DOX, an anticancer drug and prolong its release. The drug release from the 25 wt % PAU2BSA hydrogel was compared with that of original PAU2 copolymer hydrogel. FIG. 9 shows that the cumulative release of DOX from the PAU2 and PAU2BSA hydrogels persisted for 5 weeks or more without the initial burst release of drugs. The DOX release from PAU2BSA was proceeded with in a relatively slow pattern (i.e., the DOX release from the PAU2 reached >60% within 5 weeks, whereas that from the PAU2BSA reached 40% within 5 weeks). The above release profile indicates that BSA, due to its binding affinity toward drugs, helps to maintain the level of DOX loaded into the hydrogel networks. Accordingly, the conjugate hydrogel can effectively prolong the release of drugs for a long-term sustained-release.

4) Analysis of in Vitro Cytotoxicity

The cytotoxicity of hydrogels was evaluated via a direct contact method. In particular, L929 fibroblasts were used and the cells were inoculated into a 96-well plate at a seeding density of 10,000 cells per well in 0.2 mL of growth medium at 37° C. for 24 hours. Then, the growth medium was removed and then a fresh medium containing a desirable amount of polymers was added thereto. After incubating the cells for 48 hours, their metabolic activities were observed at 570 nm wavelength within the microplate reader via MTT assay.

The result of cytotoxicity evaluation of the PAU2BSA is shown in FIG. 10. FIG. 10 shows that the cell viability was >90% at a low polymer concentration (i.e., 50-300 µg/mL), whereas it was >80% and >70% at high polymer concentrations of 500 and 1000 ug/mL, respectively. Accordingly, it was confirmed that the conjugates of the present invention has no cytotoxicity and thus can be used as a biological material.

EXAMPLE 3

Preparation of PAEU-BSA Conjugates

The poly(ethylene glycol) (PEG, $M_n$=2000 and $M_n$=4600), 1,6-diisocyanate hexamethylene (HDI), dibutyltin dilaurate (DBTL), anhydrous chloroform, anhydrous dichloromethane (DCM), 1-(2-hydroxyethyl) piperazine (HP), doxombicin hydrochloride, and phosphate buffer saline (PBS) used in the experiment were purchased from Sigma-Aldrich (St. Louis, Mo., USA), and they were used in an 'as purchased' state. NaOH, HCl, diethyl ether, and n-hexane were purchased from Samchun Co. (Seoul, Korea). The other reagents were analytical grade and they were used as received without further purification.

Step 1: Synthesis of PAEU

PAEU was synthesized as shown in Reaction Scheme 3 below, using a method described in the previously reported reference (D. S. Lee et al., Soft Matter, 2011, 7, 4974-4982). The process of PAEU synthesis is briefly explained below.

and hydroxyl end groups of PEG and HPB monomers, in chloroform in the presence of DBTL as a catalyst (Reaction Scheme 3).

The synthesis of [PEG-PAEU]$_x$ copolymer (PAEU-20-2) is as follows: PEG (1 mmol) and 0.002 g of DBTL were dried in a 250 mL two neck round bottom flask maintained at 100° C. under vacuum for 2 hours. Then, the temperature was reduced to 60° C., and HPB monomers (12 mmol) was added and dried under vacuum for 30 minutes. The vacuum was replaced with dry nitrogen and 80 mL of anhydrous chloroform was added thereto. After the reactants were dissolved, HDI (12 mmol) was added thereto and the reaction was continued for additional 3 hours at 60° C. Finally, the reaction solution was concentrated via evaporation under vacuum, and precipitated in an excess of diethyl ether. The precipitated copolymers were filtered and dried under vacuum for 48 hours. The final yield was about 90%. The molecular weight of the copolymers was adjusted by changing the supply ratio of reactants and the molecular weight of PEG.

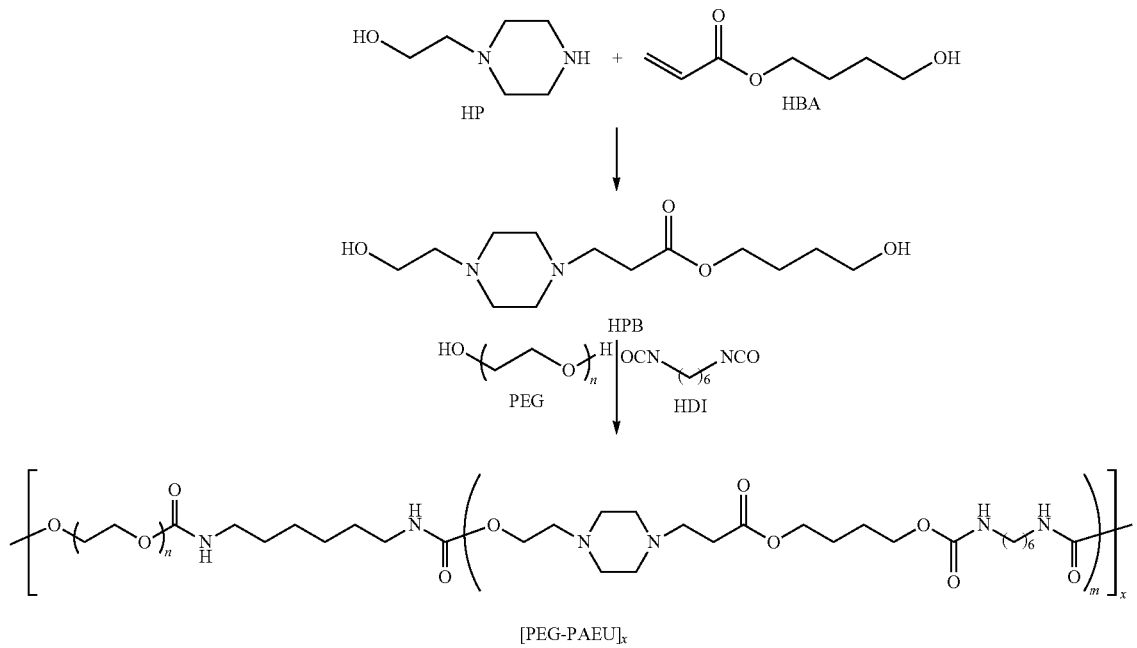

[Reaction Scheme 3]

First, amino ester dihydroxyl (HPB) monomers and copolymers thereof were synthesized and their characteristics were analyzed. The HPB monomer was synthesized via Michael addition reaction between the secondary amine group of HP and the vinyl group of HBA (Reaction Scheme 3). The details of the reaction are as follows: HP (20 mmol) was dissolved at room temperature in 40 mL of anhydrous DCM in a 250 mL round bottom flask. Then, HBA (20 mmol) was added and the flask was placed in an oil-bath maintained at 45° C. while stirring constantly for 2 hours. The reaction solution was evaporated and concentrated under vacuum and precipitated in an excess of n-hexane. The HPB monomer was filtered and dried under vacuum for 48 hours before use. The structure of the synthesized HPB monomer was confirmed via $^1$H NMR.

The multi-block copolymer [PEG-PAEU]$_x$ was synthesized via polyaddition between isocyanate groups of HDI Step 2: Preparation of Acrylated PAEU The acrylated PAEU (APAEU) was prepared from the PAEU, which was synthesized in Step 1 above, as described below.

In brief, PAEU was acrylated under argon atmosphere by reaction with acryloyl chloride and triethylamine, at a mole ratio of 1.5:1 relative to the OH group. The resulting product was precipitated in an ice-cold diethyl ether and dried in a vacuum oven for at least 48 hours. By using proton NMR ($^1$H NMR), the end group conversion (>90%) and the purity of the final product (data not shown) was confirmed.

Step 3: Synthesis of PAEU-BSA Conjugates

The conjugation between PAEU and BSA was performed by modifying a method described in the previously reported reference (L. Oss-Rosen, D. Seliktar, Acta Biomater. 2011, 7, 163) as shown in Reaction Scheme 4 below.

[Reaction Scheme 4]

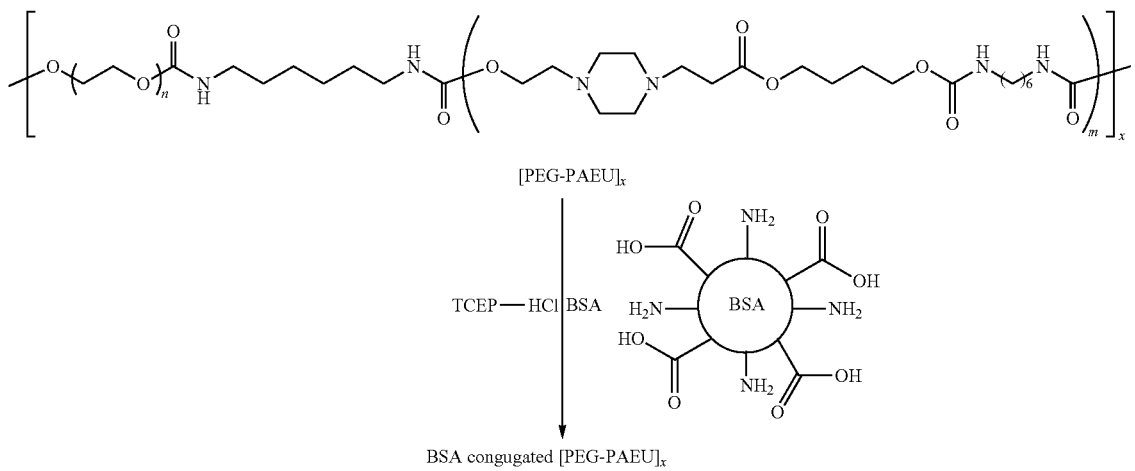

BSA congugated [PEG-PAEU]$_x$

As shown in Reaction Scheme 4 above, TCEP-HCl was added to 7 mg/mL BSA (the molar ratio of TCEP:albumin cysteines was 2:1) solution in PBS containing 8 M urea. Then, APAEU was added to the BSA solution and allowed to react at room temperature overnight (the molar ratio of APAEU:albumin cysteines was 1:1). The reactants were precipitated in acetone, redissolved in PBS containing 8 M urea, dialyzed against PBS (12-14 kDa MW cut-off, Spectrum, Gardena, Calif.) at 4° C. for two days, lyophilized to obtain a conjugate (PAEUBSA) before its later use.

Experimental Example 3

Analysis of Characteristics of Conjugates of the Present Invention

The characteristics of the PAEU-BSA conjugates prepared in Example 3 were analyzed as described below.
1) Characterization by FT-IR and SDS-PAGE The copolymers and the conjugates were characterized by FT-IR.

The conjugates exhibited a noticeable absorption corresponding to the N—H stretching vibration at 3421 cm$^{-1}$ of BSA molecules. The absorption bands shown at 1656 cm$^{-1}$ and 1533 cm$^{-1}$, i.e., amide I (AI, a C=O stretching vibration) and amide II (AII, a C—N stretching vibration and a N—H bending vibration) bands are typically recognized as characteristic bands for protein characterization. The spectrum of the copolymers exhibited absorptions at 3338 cm$^{-1}$, 1695 cm$^{-1}$, 1265 cm$^{-1}$, and 1101 cm$^{-1}$, which respectively expressed the N—H stretching of HPB, the C=O stretching of urethane, the C—N stretching of HPB aromatic, and the C—O—C stretching of PEG. The conjugation was also confirmed via SDS-PAGE, in addition to the FT-IR result. As a result, the successful conjugation between the copolymers and BSA was confirmed.
2) Sol-gel Phase Transition Behavior According to pH and Temperature The sol-gel phase transition behavior of the PAEU copolymers prepared in Example 3 in an aqueous solution was measured by the test tube inverting method.

First, each sample was dissolved in PBS at pH 4 within a 5 mL, vial tube at a predetermined concentration, and the sol-gel phase transition behavior according to pH was measured while adjusting the pH of the solution to a desirable pH using NaOH and HCl. The sol-gel transition was confirmed by observing that the sample did not flow when the vial was turned upside down.

Additionally, the sol-gel phase transition behavior according to temperature was measured by a method which includes placing a vial containing about 0.5 mL of a solution into a temperature-controlled water bath, being heated at temperature intervals of 2° C., and maintaining equilibrium for 10 minutes. The sol-gel transition was confirmed by observing that the sample did not flow when the vial was turned upside down.

The sol-gel phase diagrams of the PAEU copolymers prepared in Example 3 are shown in FIG. 11.

As seen in FIG. 11, the PAEU copolymers prepared in Example 3 exhibited a sol-gel phase transition behavior responding to pH and temperature, and in particular, they were shown to be converted to a gel at 37° C. and pH 7.4 of the physiological conditions.
3) In Vitro and In Vivo Gel Degradation Behavior The in vitro and in vivo gel degradation behaviors of the PAEU copolymers prepared in Example 3 were analyzed and the results are shown in FIG. 12.

As seen in FIG. 12, it was confirmed that the PAEU copolymers prepared in Example 3 could remain in vitro and in vivo without being completely decomposed for a month or more.
4) In Vivo Release In order to examine the in vivo release of lysozyme, a sample solution loaded with 250 μL of lysozyme was injected to male SD rats (three rats per group). At predetermined times, blood samples were collected from the caudal vein, centrifuged to obtain blood sera, and stored them at −21° C. until the next analysis. The concentration of the lysozyme in the blood sera was measured using a commercial lysozyme (LZM) ELISA kit (Cusabio, China).

The results are shown in FIG. 13.

As seen in FIG. 13, the PAEU-BSA conjugates prepared in Example 3 reduced the initial burst release of lysozyme compared to the PAEU copolymers, and sustained the lysozyme release for two weeks or more.

EXAMPLE 4

Preparation of PAEU-BSA Conjugates

Step 1: Synthesis of PAEU

PAEU was synthesized as shown in Reaction Scheme 5 below, using a method described in a previously reported reference (D. S. Lee et al., Soft Matter, 2011, 7, 4974-4982). The process of PAEU synthesis is briefly explained below.

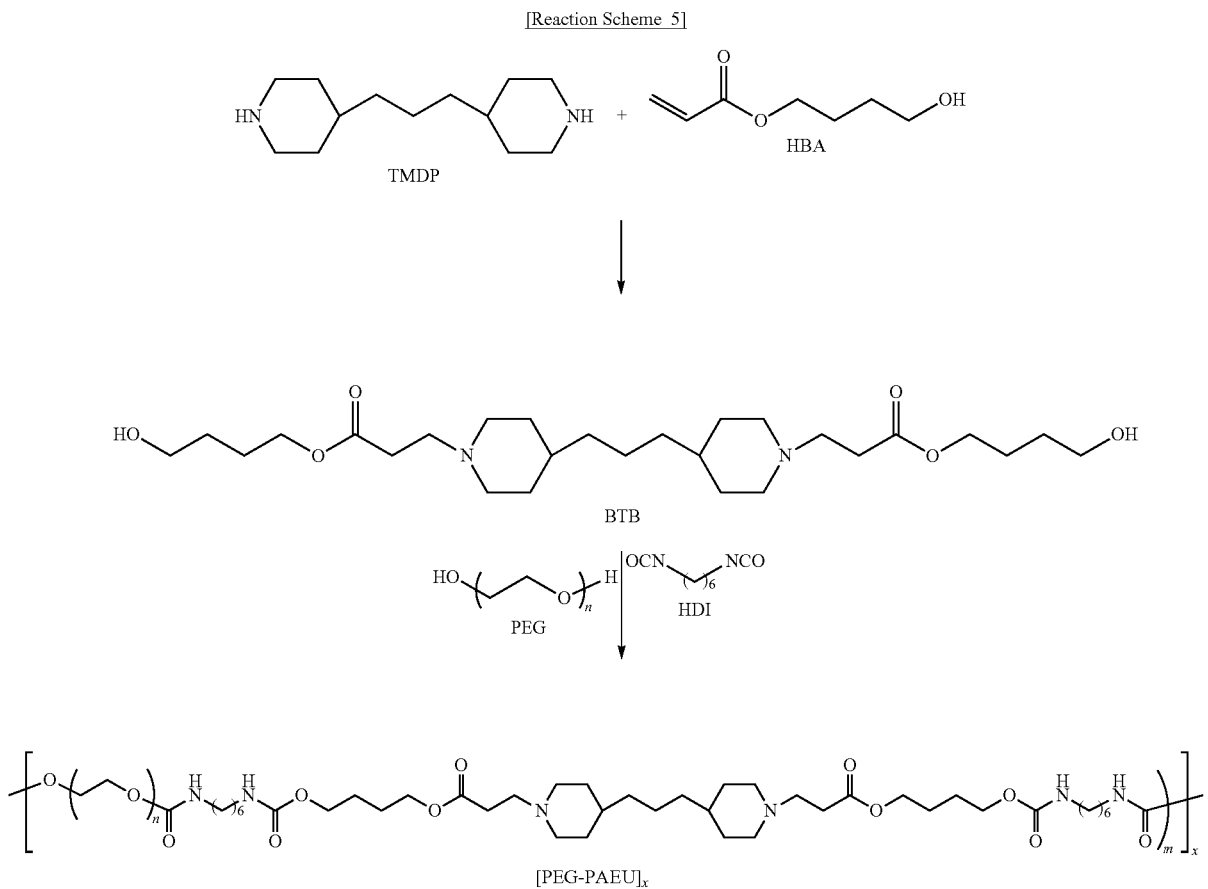

[Reaction Scheme 5]

The BTB monomer was synthesized via Michael addition reaction between the secondary amine group of TMDP and the vinyl group of HBA (Reaction Scheme 5). The details of the reaction are as follows.

First, TMDP (40 mmol) was dissolved at room temperature in 40 mL of anhydrous DCM in a 250 mL round bottom flask. Then, HBA (20 mmol) was added thereto and the flask was placed in an oil-bath maintained at 45° C. while stirring constantly for 2 hours. The reaction solution was evaporated and concentrated under vacuum and precipitated in an excess of n-hexane to obtain BTB monomers. Polyethylene glycol (2 mmol) and dibutyltin diaurate (0.002 g) were placed in a round bottom flask, and dried under vacuum at 100° C. for 2 hours to remove water.

After reducing the flask temperature to 50° C., BTB (20 mmol) was added thereto and dried under vacuum for 30 minutes. While releasing vacuum, nitrogen gas was added thereto, and then 80 mL of anhydrous chloroform was added to completely dissolve the reactants, and 1,6-hexamethylene diisocyanate (HDI) (21 mmol) was added and reacted at room temperature for 30 minutes. Then, the reaction temperature was increased to 60° C. and a urethane reaction was performed for 3 hours. The resulting product was cooled to room temperature, and precipitated in an excess of ethyl ether and filtered to remove unreacted materials to obtain polyethylene glycol-poly(amino urethane) multi-block copolymer.

Step 2: Preparation of Acrylated PAEU

Acrylated PAEU (APAEU) was prepared from the PAEU synthesized in Step 1 above as described below.

In brief, PAEU was acrylated under argon atmosphere by reaction with acryloyl chloride and triethylamine, at a mole ratio of 1.5:1 relative to the OH group. The resulting product was precipitated in an ice-cold diethyl ether and dried in a vacuum oven for at least 48 hours. By using proton NMR ($^1$H NMR), the end group conversion (>90%) and the purity of the final product (data not shown) was confirmed.

Step 3: Synthesis of PAEU-BSA Conjugate

The conjugation between PAEU and BSA was performed by modifying a method described in the previously reported reference (L. Oss-Rosen, D. Seliktar, *Acta Biomater* 2011, 7, 163) in Reaction Scheme 6 as shown below:

[Reaction Scheme 6]

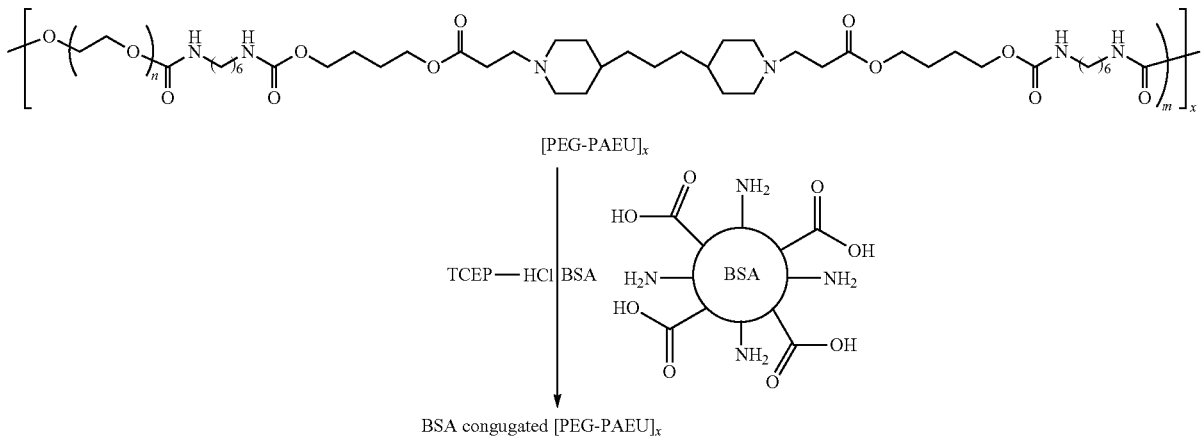

As shown in Reaction Scheme 6 above, TCEP-HCl was added to 7 mg/mLBSA (the molar ratio of TCEP:albumin cysteines was 2:1) solution in PBS containing 8 M urea. Then, APAEU was added to the BSA solution and allowed to react at room temperature overnight (the molar ratio of APAEU:alburnin cysteines was 1:1). The reactants were precipitated in acetone, redissolved in PBS containing 8 M urea, dialyzed against PBS (12-14 kDa MW cut-off, Spectrum, Gardena, Calif.) at 4° C. for two days, lyophilized to obtain a conjugate (PAEUBSA) before its later use.

Experimental Example 4

Analysis of Characteristics of Conjugates of the Present Invention

The characteristics of the PAEU-BSA conjugates prepared in Example 4 were analyzed as described below.
1) Characterization by FT-IR and SDS-PAGE
The copolymers and the conjugates were characterized by FT-IR.
The conjugates exhibited a noticeable absorption corresponding to the N—H stretching vibration at 3421 $cm^{-1}$ of BSA molecules. The absorption bands shown at 1656 $cm^{-1}$ and 1533 $cm^{-1}$, i.e., amide I (AI, a C=O stretching vibration) and amide II (AII, a C—N stretching vibration and a N—H bending vibration) bands are typically recognized as characteristic bands for protein characterization. The spectrum of the copolymers exhibited absorptions at 3338 $cm^{-1}$, 1695 $cm^{-1}$, 1265 $cm^{-1}$, and 1101 $cm^{-1}$, which respectively expressed the N—H stretching of HPB, the C=O stretching of urethane, the C—N stretching of HPB aromatic, and the C—O—C stretching of PEG. The conjugation was also confirmed via SDS-PAGE, in addition to the FT-IR result. As a result, the successful conjugation between the copolymers and BSA was confirmed.
2) Sol-gel Phase Transition Behavior According to pH and Temperature
The sol-gel phase transition behavior of the PAEU and PAEUBSA conjugates in an aqueous solution was measured by the test tube inverting method.
First, each sample was dissolved in PBS at pH 4 within a 5 mL vial tube at a predetermined concentration, and the sol-gel phase transition behavior according to pH was measured while adjusting the pH of the solution to a desirable pH using NaOH and HCl. The sol-gel transition was confirmed by observing that the sample did not flow when the vial was turned upside down.
Additionally, the sol-gel phase transition behavior according to temperature was measured by a method which includes placing a vial containing about 0.5 mL of a solution into a temperature-controlled water bath, being heated at temperature intervals of 2° C., and maintaining equilibrium for 10 minutes. The sol-gel transition was contained by observing that the sample did not flow when the vial was turned upside down.
As a result, the PAEU and PAEUBSA conjugates exhibited sol-gel phase transition behaviors responding to pH and temperature, and in particular, they were shown to be converted to a gel at 37° C. and pH 7.4 of the physiological conditions (data not shown).
3) In Vitro and In Vivo Gel Degradation Behavior
The in vitro and in vivo gel degradation behaviors of the PAEU copolymers prepared in Example 4 were analyzed.
As a result, it was confirmed that the PAEU copolymers prepared in Example 4 could remain in vitro and in vivo without being completely decomposed for a month or more (data not shown).
4) In Vivo Release
In order to examine the in vivo release of lysozyme, a sample solution loaded with 250 μL of lysozyme was injected to male SD rats (three rats per group). At predetermined tunes, blood samples were collected from the caudal vein, centrifuged to obtain blood sera, and stored them at −21° C. until the next analysis. The concentration of the lysozyme in the blood sera was measured using a commercial lysozyme (LZM) ELISA kit (Cusabio, China).
As a result, the PAEU-BSA conjugates prepared in Example 4 reduced the initial burst release of lysozyme, and sustained the lysozyme release for two weeks or more (data not shown).
From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents and other embodiments that may be included within the spirit and scope of the present invention as defined by the appended claims.

The invention claimed is:

1. A conjugate of albumin and a temperature- and pH-sensitive multi block copolymer, wherein the multi-block copolymer is conjugated to the albumin, and the multi-block copolymer has a number average molecular weight from 10,000 g/mol to 25,000 g/mol and has repeating units of Chemical Formula 1:

[Chemical Formula 1]

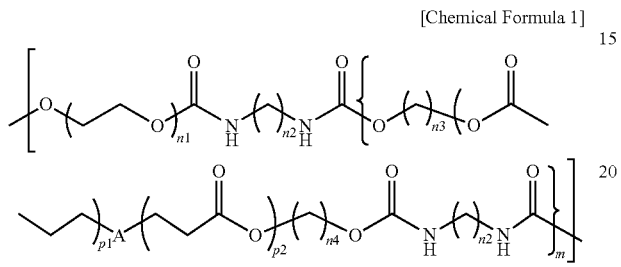

wherein, in the above formula,

A is

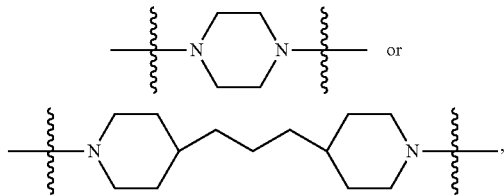

n1 is an integer from 5 to 50,
n2 is an integer from 2 to 8,
n3 is an integer from 1 to 10,
n4 is an integer from 1 to 10,
p1 is 0 or 1,
p2 is 0 or 1, and
m is an integer from 2 to 6, and
wherein a solution of the conjugate exhibits a sol-gel transition temperature dependent on pH and temperature of the solution.

2. The conjugate of claim 1, wherein n2 is 6.

3. The conjugate of claim 1, wherein n3 is 2.

4. The conjugate of claim 1, wherein the multi-block copolymer is conjugated to the albumin via a linker of Chemical Formula 5 below:

[Chemical Formula 5]

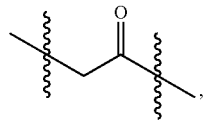

wherein the linker is formed by introducing acryloyl groups to the multi-block copolymer to attach carbonyl moieties of the acryloyl groups at polyethylene glycol block ends of the copolymer; reducing the albumin to form thiol groups at the surface thereof; and reacting vinyl moieties of the acryloyl groups with thiol groups on the surface of the reduced albumin to form a single bond.

5. The conjugate of claim 1, wherein the conjugate has a molar ratio of the multi-block copolymer to albumin cysteines from 1:1 to 1:10.

6. A method for preparing a conjugate of albumin and a temperature- and pH-sensitive multi-block copolymer, wherein the multi-block copolymer is conjugated to the albumin, and the multi-block copolymer has a number average molecular weight from 10,000 g/mol to 25,000 g/mol and has repeating units of Chemical Formula 1:

[Chemical Formula 1]

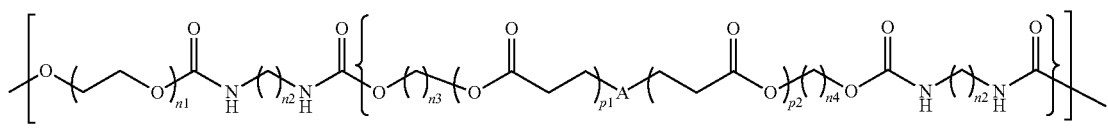

wherein, in the above formula,
A is

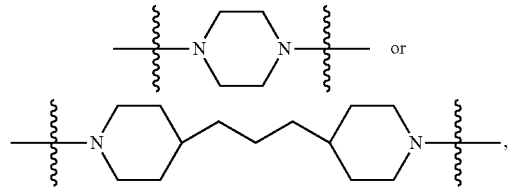

n1 is an integer from 5 to 50,
n2 is an integer from 2 to 8,
n3 is an integer from 1 to 10,
n4 is an integer from 1 to 10,
p1 is 0 or 1,
p2 is 0 or 1,
m is an integer from 2 to 6, and
wherein a solution of the conjugate exhibits a sol-gel transition temperature dependent on pH and temperature of the solution, the method comprising:
preparing a multi-block copolymer, which has a number average molecular weight from 10,000 g/mol to 25,000 g/mol and has repeating units of Chemical Formula 1, by reacting a compound of Chemical Formula 2 below, a compound of Chemical Formula 3 below, and a compound of Chemical Formula 4 below (step 1);
preparing an acrylated multi-block copolymer by reacting the multi-block copolymer with acryloyl halide (step 2); and
reacting albumin with a thiol reducing agent and then reacting the reduced albumin with the acrylated multi-block copolymer (step 3):

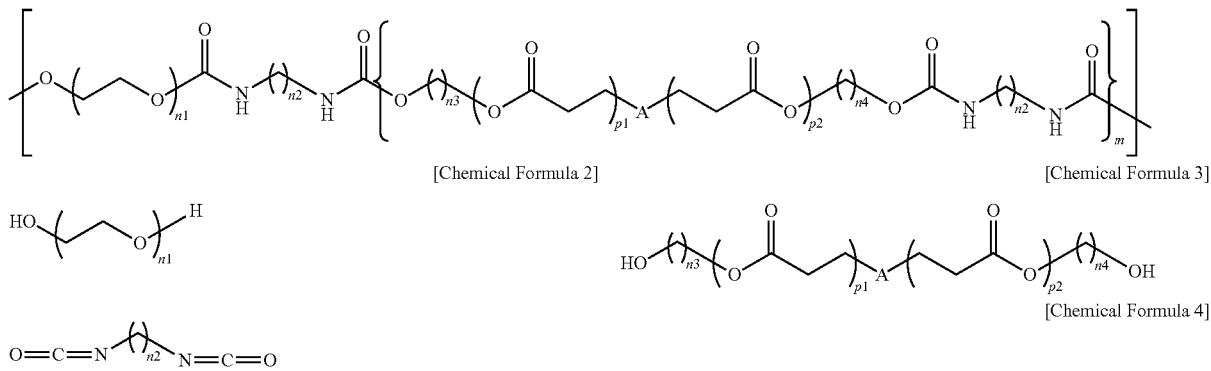

[Chemical Formula 1]

[Chemical Formula 2]

[Chemical Formula 3]

[Chemical Formula 4]

wherein, in the above formulas,
A is

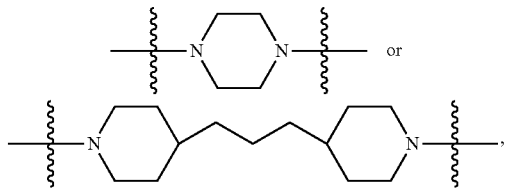

$n1$ is an integer from 5 to 50,
$n2$ is an integer from 2 to 8,
$n3$ is an integer from 1 to 10,
$n4$ is an integer from 1 to 10,
$p1$ is 0 or 1,
$p2$ is 0 or 1, and
$m$ is an integer from 2 to 6.

7. The method of claim 6, wherein the reaction of step 1 is performed in the presence of a catalyst selected from the group consisting of dibutyltin dilaurate, stannous octoic acid, stannous chloride, iron oxide, aluminum triisopropoxide, $CaH_2$, Zn, and lithium chloride.

8. The method of claim 6, wherein the molar ratio among the compound of Chemical Formula 2, the compound of Chemical Formula 3, and the compound of Chemical Formula 4 is in the range from 1:5:10 to 1:10:15.

9. The method of claim 6, wherein the reaction of step 1 is performed at a temperature from 40° C. to 80° C.

10. The method of claim 6, wherein the reaction of step 3 is performed in a molar ratio of the acrylated multi-block copolymer to albumin cysteines from 1:1 to 1:10.

11. A sustained-release drug carrier comprising a conjugate according to claim 1.

12. The sustained-release drug carrier of claim 11, wherein the drug carrier comprises a drug which is paclitaxel, doxorubicin, docetaxel, chlororambucil, insulin, exendin-4, human growth hormone, erythropoietin, granulocyte colony stimulating factor (G-CSF), granulocyte-macrophage stimulating factor (GM-CSF), lysozyme, bovine serum albumin, antimicrobial agents, steroids, antiinflammatory analgesic agents, sex hormones, immunosuppressants, antiviral agents, anesthetic agents, antiemetics or antihistamines.

13. The sustained-release drug carrier of claim 11, wherein the drug carrier is in the form of an injectable hydrogel.

14. The sustained-release drug carrier of claim 11, wherein the drug carrier has a sustained release profile over a period of 2 weeks to 5 weeks.

* * * * *